United States Patent
Ryan et al.

(10) Patent No.: US 7,357,799 B2
(45) Date of Patent: Apr. 15, 2008

(54) THERMAL COAGULATION USING HYPERCONDUCTIVE FLUIDS

(75) Inventors: Thomas P. Ryan, Flemington, NJ (US); Martin A. Reynolds, Mansfield, MA (US); Hassan Serhan, South Easton, MA (US); Anthony Coston, Sergentsville, NJ (US)

(73) Assignee: Depuy Acromed, Inc., Raynham, MA (US)

( * ) Notice: Subject to any disclaimer, the term of this patent is extended or adjusted under 35 U.S.C. 154(b) by 168 days.

(21) Appl. No.: 10/457,088

(22) Filed: Jun. 6, 2003

(65) Prior Publication Data
US 2004/0002746 A1 Jan. 1, 2004

Related U.S. Application Data

(60) Provisional application No. 60/391,848, filed on Jun. 27, 2002.

(51) Int. Cl.
*A61B 18/14* (2006.01)
(52) U.S. Cl. ............... 606/32; 606/49; 606/50
(58) Field of Classification Search ........... 128/898; 606/32, 34, 41, 46, 49, 50; 607/99, 105, 607/113; 604/35, 114
See application file for complete search history.

(56) References Cited

U.S. PATENT DOCUMENTS

| | | | |
|---|---|---|---|
| 4,381,007 A * | 4/1983 | Doss | 606/27 |
| 5,433,739 A | 7/1995 | Sluijter et al. | |
| 5,919,189 A * | 7/1999 | Benderev | 606/45 |
| 6,015,406 A | 1/2000 | Goble et al. | |
| 6,099,514 A | 8/2000 | Sharkey et al. | |
| 6,264,650 B1 | 7/2001 | Hovda et al. | |
| 6,402,742 B1 * | 6/2002 | Blewett et al. | 606/34 |
| 6,529,756 B1 * | 3/2003 | Phan et al. | 600/374 |
| 2005/0059966 A1 * | 3/2005 | McClurken et al. | 606/45 |

FOREIGN PATENT DOCUMENTS

| | | |
|---|---|---|
| EP | 0 878 167 A2 | 11/1998 |
| WO | WO 00 09053 A | 2/2000 |
| WO | WO 00/71043 A1 | 11/2000 |

OTHER PUBLICATIONS

Yi Miao, MD et al.; A Comparative Study on Validation of a Novel Cooled-Wet Electrode for Radiofrequency Liver Ablation; Investigative Radiology; vol. 35, No. 7, 438-444; © 2000, Lippincott Williams & Wilkins, Inc.

S. Nahum Goldberg, MD et al.; Ratio-Frequency Thermal Ablation with NaCl Solution Injection: Effect of Electrical Conductivity on Tissue Heating and Coagulation—Phantom and Porcine Liver Study; RADIOLOGY; Apr. 2001; 219:157-165.

* cited by examiner

*Primary Examiner*—Lee S. Cohen

(57) ABSTRACT

This invention relates to the use of hyperconductive fluids to coagulate tissue within the intervertebral disc.

43 Claims, 11 Drawing Sheets

THERMAL COAGULATION USING HYPERCONDUCTIVE FLUIDS

This application claims priority from co-pending U.S. Provisional Patent Application No. 60/391,848, filed Jun. 27, 2002, entitled "Thermal Coagulation Using Hyperconductive Fluids".

BACKGROUND OF THE INVENTION

U.S. Pat. No. 6,264,650 ("Hovda") discloses methods for therapeutically applying electrical energy to tissue within a patient's spine, including introducing an active electrode into the patient's spine, positioning an active electrode near a target tissue, and applying a high voltage across the electrode to produce a plasma to volumetrically remove or ablate the target tissue.

Hovda is primarily directed to ablation techniques, such as laminectomy/discectomy procedures, wherein problematic tissue is removed or ablated. However, Hovda also discloses methods for shrinking collagen tissue. In particular, Hovda discloses treating fissure or tears within the inner wall of the annulus fibrosus of a degenerative disc by applying a voltage across the electrodes to heat the fissure and shrink the collagen fibers, thereby creating a seal or weld within the inner wall of the annulus fibrosus. See Hovda at col. 10, line 64.

In some embodiments, Hovda discloses delivering a conductive fluid to the target site to substantially surround the active electrode with a conductive media. Hovda teaches that this conductive fluid should have a threshold conductivity to provide a suitable conductive path between the return electrode and the electrode terminal. Although Hovda repetitively discloses the use of isotonic or normal saline as the conductive fluid, Hovda also teaches that a more conductive fluid, or one with a higher ionic concentration, will usually provide a more aggressive ablation rate, and reports that a saline solution with higher levels of sodium chloride than conventional saline (which is on the order of about 0.9% sodium chloride), e.g., on the order of greater than 1% or between about 3% and about 20%, may be desirable. See Hovda at col. 19, line 31.

In most heating embodiments in Hovda, Hovda teaches heating the target tissue by passing the radiofrequency ("RF") current through the target tissue, wherein the tissue's resistance to the current produces the desired heating. However, in one embodiment, Hovda further teaches first passing the RF current through a conductive fluid to resistively heat the conductive fluid, and then directing the heated conductive fluid to the target tissue. In this embodiment, Hovda teaches that the primary mechanism for imparting energy to the tissue is the heated fluid, rather than the electric current. See Hovda at col. 13, line 28, and col. 39, line 14.

Hovda teaches many methods of changing the depth of the heating within a tissue, including a) changing the power level of the apparatus, b) adding a resistor to the device, c) adding a voltage reducing element to the device, d) changing the frequency of the RF current, and e) changing the electrode diameter.

In one embodiment, Hovda discloses increasing the temperature of the target tissue to 60° C. at a depth of 1-5 mm by either direct heating (i.e., deep penetration of current) or by heating indirectly (exposure to an RF heated fluid). See Hovda at col. 13, line 32. Hovda repeatedly teaches that the depth of penetration of the thermal damage is typically less than 5 mm. See Hovda at col. 10, line 47; col. 13, line 28; col. 30, line 47; and col. 38, line 25.

In one embodiment, Hovda teaches that the conductive fluid between the active and return electrodes will generally minimize current flow into the surrounding tissue. Thereby minimizing thermal damage to the tissue, so that severed blood vessels on the surface of the hole may not be coagulated as the electrodes advance through the tissue. Therefore, in this embodiment, Hovda teaches that the presence of the conductive fluid also essentially acts as an electrical short that keeps the surrounding tissue cool. See Hovda at col. 16, line 21.

Hovda further teaches that low impedance pathways provide low heating levels. See Hovda at col. 17, line 37.

In sum, Hovda discloses using isotonic saline for both ablation and more mild electrosurgical techniques such as tissue coagulation and teaches the use of hypertonic saline only for more severe ablation procedures.

U.S. Pat. No. 6,099,514 ("Oratec") discloses a method of treating interverterbal discs by resistively heating. Oratec discloses the use of normal or isotonic saline.

U.S. Pat. No. 6,015,406 ("Goble") discloses an electrode-containing electrosurgical instrument for treating tissue in the presence of an electrically-conductive fluid ("ECF") medium. Goble discloses only normal saline as the electrically-conductive fluid medium.

US Pat. No. 5,433,739 ("Sluitjer") discloses a method of therapeutically treating the disc by heating the inside of the disc with RF energy, microwave current, resistive heating and heating by ferromagnetic seeds. Sluijter characterizes the disc as "consisting of a fibrous structure with a substantially low electrical impedence."

Goldberg et al., Radiology April 2001, 219(1), pp. 157-165, ("Goldberg") reports on the effects of NaCl concentration on tissue conductivity, radiofrequency (RF) deposition, and heating in phantom models, and further teaches optimization of an adjunctive NaCl solution injection for RF ablation in an in vivo model. In the phantom models, Goldberg reports that NaCl concentration has significant but non-linear effects on electrical conductivity and RF deposition, and observed progressively greater heating up to 5.0% NaCl, with reduced temperatures at higher concentrations. In the in vivo studies upon normal well-perfused liver, maximum coagulation (7.0 cm) was observed to occur with injection of small amounts of saturated (38%) NaCl solution. Goldberg concluded that injection of NaCl solution before RF ablation can increase energy deposition, tissue heating, and induced coagulation, which will likely benefit clinical RF ablation.

However, Goldberg also reported the existence of non-uniform NaCl concentration in some of the models. Since Goldberg is concerned with tumor ablation, Goldberg found this uncontrolled non-uniform concentration to be an undesirable feature. Therefore, Goldberg suggests that one drawback to using hypertonic NaCl levels was a possible inability to control the uniformity of its distribution.

In addition, Goldberg reported that HCF can significantly migrate within collagen-based tissue to the point where it crossed a tissue boundary from the liver to the gall bladder. Therefore, Goldberg suggests that another drawback to using hypertonic NaCl levels was a possible inability to control its migration.

In sum, Goldberg was concerned mostly with eradicating tumors, and found that "the extent of tissue heating and coagulation were significantly influenced by both the volume and concentration of the NaCl solution injected." However, Goldberg further cited concerns as to the possible inability to control the distribution and migration of the injected HCF. Goldberg concluded that "it will be important to determine whether the strategy of injecting NaCl solutions can alter tissue coagulation in a predictable and reproducible fashion so that the volume of coagulation induced can be appropriately matched to tumor size and location.

SUMMARY OF THE INVENTION

The present inventors believe that although the use of isotonic saline as an electroconductive fluid for coagulation (as disclosed by Hovda) may desirably provide a uniform and reproducible electrical path for delivering an RF current to a target tissue to resisitively heat the target tissue, its marginal electrical conductivity (about the same as the target tissue) does not provide any substantially preferential pathway for the current than normal tissue, nor a substantially greater acceptance of power than normal tissue. Accordingly, when isotonic saline is used as the electroconductive fluid ("ECF") for coagulating fissures, the healthy tissue surrounding the fissured tissue will be as preferred an electrical pathway as the isotonic saline in the fissure, will accept power substantially equally as the isotonic saline in the fissure, will experience substantially the same temperature rise as the isotonic saline in the fissure, and will experience substantially the same level of coagulation as the tissue closely adjacent the fissure. Thus, the undesired and electrically inefficient damage to healthy tissue is a drawback of using isotonic saline as an ECF in fissure welding procedures.

Now referring to FIG. 1, the present inventors have recognized the desirability of exposing fissures 11 in the annulus wall 13 of an intervertebral disc 15 to hyperconductive fluids ("HCF") 17 such as hypertonic saline. When a HCF is so used, it enters the breach in the annular wall caused by the fissure, but does not substantially penetrate the intact portions of the annular wall. The presence of the HCF by the annular wall fissures creates a non-uniform distribution of HCF within the annulus fibrosus 18 wherein the HCF is present substantially only in the vicinity of the fissures. Now referring to FIG. 2, because the HCF has a significantly higher electrical conductivity than the adjacent healthy collagen tissue regions 16, when a voltage is applied between first 21 and second 23 electrodes, the RF current 25 produced thereby will preferentially pass through the HCF 27 and therefore cause its preferential heating. The heated HCF may then conductively heat only the tissue regions closely adjacent the fissured portions of the annulus. The preferential heating in the vicinity of the fissured portions of the annulus allows the clinician to heat substantially only the target tissue to the desired coagulation or denervation endpoint, thereby substantially avoiding damage to the adjacent healthy tissue.

Therefore, in accordance with one embodiment of the present invention, there is provided a method of therapeutically treating an intervertebal disc having an annulus fibrosus having a fissure defining first and second closely adjacent collagen tissue regions, comprising the steps of:
a) adding a hyperconductive fluid to the fissure,
b) positioning a first electrode adjacent to the hyperconductive fluid,
c) applying a sufficiently high frequency voltage difference between the first electrode and a second electrode to generate a current flowing preferentially through the hyperconductive fluid.

Preferably, first electrode 21 is located within 1 mm of the outer wall of the annulus fibrosus and more preferably is in contact with the outer wall. Also preferably, second electrode 23 is located within 1 mm of the mouth of the fissure and is preferably located within the mouth of the fissure.

In addition, since the hyperconductive fluid ("HCF") has a higher electrical conductivity, it can accept more power than isotonic saline and so can be heated more quickly to higher temperatures than isotonic saline. Without wishing to be tied to a theory, the HCF may behave as a virtual electrode that expands the local influence of the actual electrode, thereby leading to an improved penetration of power within the region containing the HCF. The resistively heated HCF can then conductively heat the closely adjacent collagen tissue regions surrounding the fissure.

Therefore, in accordance with one embodiment of the present invention, there is provided a method of therapeutically treating an intervertebal disc having an annulus fibrosus having a fissure defining first and second closely adjacent collagen tissue regions, comprising the steps of:
a) adding a hyperconductive fluid to the fissure,
b) positioning a first electrode adjacent to the hyperconductive fluid,
c) applying a sufficiently high frequency voltage difference between the first electrode and a second electrode to generate an increased current flowing through the hyperconductive fluid to preferentially resistively heat the HCF.

In addition, since the HCF has a higher electrical conductivity, the overall resistance of the circuit formed by the current passing between the electrodes is lower, thereby allowing each part of the circuit to accept more power. Accordingly, the in-line tissue that is part of the circuit experiences an increased current flow and so accepts more power. Accordingly, the in-line tissue can be resistively heated more quickly to higher temperatures and greater depths.

Therefore, in accordance with one embodiment of the present invention, there is provided a method of therapeutically treating an intervertebal disc having an annulus fibrosus having a fissure defining first and second adjacent collagen tissue regions, comprising the steps of:
a) adding a hyperconductive fluid to the fissure,
b) positioning a first electrode adjacent to the hyperconductive fluid,
c) applying a sufficiently high frequency voltage difference between the first electrode and a second electrode to generate an increased current flowing through the adjacent collagen tissue regions.

In sum, the selective and superior heating of tissue closely adjacent a fissure provided by the present invention is superior to the technique taught by Hovda because Hovda's use of isotonic saline for coagulation procedures does not provide significant electrical conductivity differentiation between the fissures and the healthy annulus tissue to produce substantially selective heating of only the fissured tissue, nor does it provide a method of quickly heating tissue to coagulation temperatures.

Therefore, in accordance with one embodiment of the present invention, there is provided a method of therapeutically treating an intervertebal disc having a nucleus pulposus and an annulus fibrosus having a fissure having a width and defining first and second adjacent collagen tissue regions, comprising the steps of:
a) adding a hyperconductive fluid to the fissure,
b) positioning a first electrode adjacent to the hyperconductive fluid,
c) applying a sufficiently high frequency voltage difference between the first electrode and a second electrode to generate a current through the hyperconductive fluid sufficient to therapeutically treat at least a portion of the adjacent collagen tissue regions.

Also in accordance with one embodiment of the present invention, there is provided a method of increasing the electrical conductivity of a fissure in an annulus fibrosus of an intervertebral disc, comprising the step of:

a) adding a hyperconductive fluid to the fissure.

DETAILED DESCRIPTION OF THE INVENTION

Figure 1:
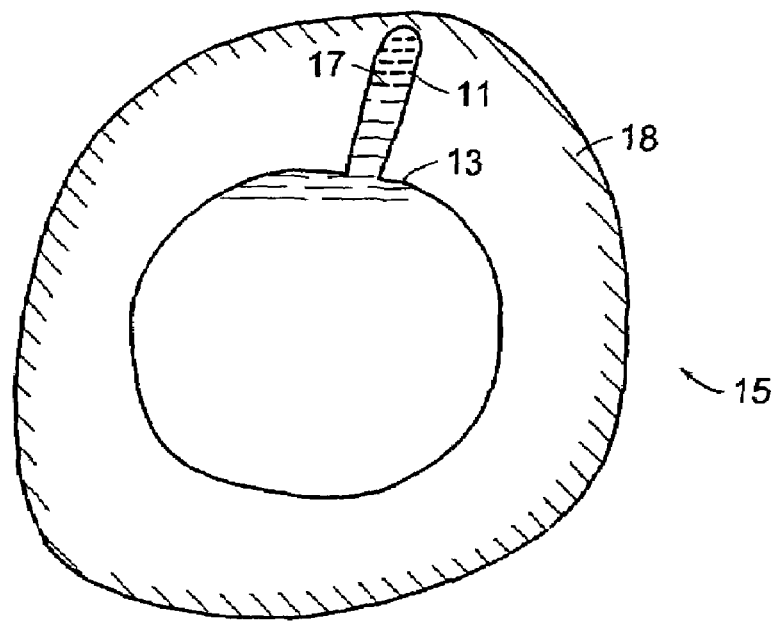
FIG. 1 is a representation of HCF present within an annular wall fissure, creating a non-uniform distribution of HCF within the annulus wherein the HCF is present substantially only in the vicinity of the fissure.
Figure 2:
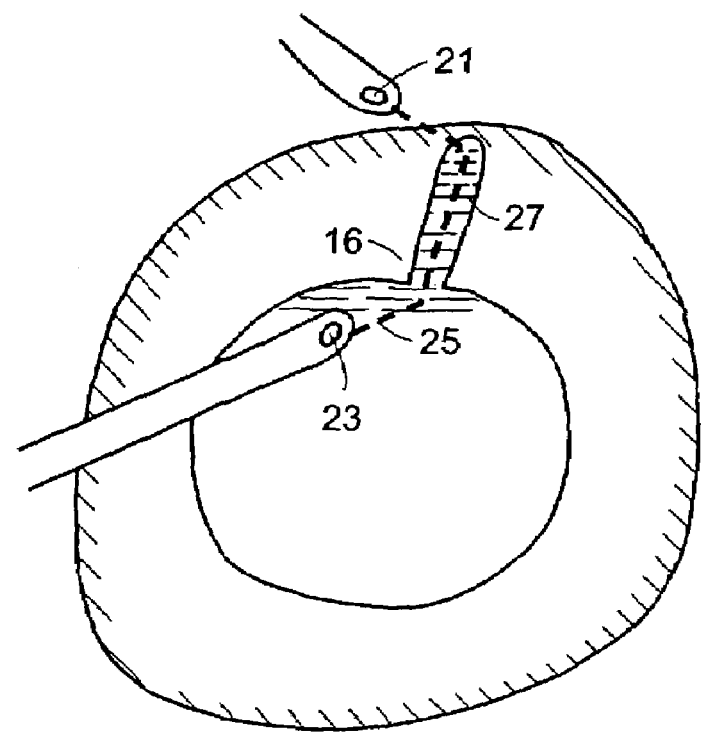
FIG. 2 is a representation of preferential heating in the vicinity of the fissured portions of the annulus, thereby allowing the surgeon to heat substantially only the target tissue to the desired coagulation endpoint, thereby substantially avoiding damage to the adjacent healthy tissue.

For the purposes of the present invention, the term "ablation" refers to volumetric removal, cutting and molecular dissociation. Ablation does not include coagulation, collagen shrinkage, welding, or denervation. "Coagulation" and "welding" are used interchangeably herein. A "hyperconductive fluid" is any fluid having an electrical conductivity exceeding that of isotonic saline. "Adjacent" bodies includes, but is not limited to, bodies that are in contact. The "inner region" of the nucleus pulposus is the inner radial 50% of the plane defined by the anteroposterior and mediolateral axes. The "outer region" of the nucleus pulposus is the outer radial 50% of the plane defined by the anteroposterior and mediolateral axes. "Electrode spacing" is the shortest distance between a first electrode and a second electrode. "Fissure" includes a partial tear, a complete tear extending completely through the wall, a surgically-made hole, and the deformation of the annulus wall associated with a bulging disc. "Therapeutically treating" collagen tissue includes coagulating the tissue and/or denervating the tissue, but does not include ablating the tissue.

In preferred embodiments, a HCF is added to a fissure. Preferred embodiments of the present invention may employ any type of conductive fluid having a conductivity greater than that of isotonic saline, which has a conductivity (in units of milliSiemans per centimeter or mS/cm) of about 17 mS/cm. Preferably, the HCF of the present invention fluid should be suitable for use in the human body, and in particular within the intervertebral disc.

In some embodiments, the hyperconductive fluid comprises water. However, in other embodiments, the hyperconductive fluid may comprise an organic fluid carrier. The HCF may be either a polar or non-polar liquid, but is preferably polar.

More preferably, the HCF is aqueous and further comprises a salt. More preferably, the aqueous HCF comprises between 1% and 38% salt, more preferably between 3% and 20%, most preferably between 20% and 38%. Preferably, the salt comprises a first species selected from the group Na, K, Ca and Mg, and mixtures thereof. More preferably, the first species is Na. Preferably, the salt comprises a second species selected from the group consisting of Cl and $SO_4$, and mixtures thereof. More preferably, the second species is Cl. In one preferred embodiment, the salt is NaCl. In another, it is KCl. In other embodiments, the HCF may comprise Ringer's solution (preferably, lactated Ringer's solution).

When the HCF comprises hypertonic saline, the hypertonic saline should be administered in a concentration and volume that provides a salt concentration in the fissured portion of between 1 and 10%, more preferably between 2% and 6%, more preferably between 3% and 5%.

Typically, the hyperconductive fluid is administered in an amount of between 1 cc and 2 cc. When the amount is less than 1 cc, there may not be an appreciable change in the conductivity of the fluid within the fissure. When the amount is more than about 2 cc, the added volume may, without more, adversely affect the pressure within the disc.

In some embodiments, the addition of the HCF to the disc may undesirably increase the fluid pressure within the disc and cause increased pain. In such situations, it is desirable to remove a portion of native disc material, preferably a portion of the nucleus pulposus.

Accordingly, in accordance with the present invention, there is provided a method of therapeutically treating a target tissue within an intervertebral disc, comprising the steps of:

a) removing a portion of the nucleus pulposus, and
b) injecting an electrically conductive fluid into the nucleus pulposus.

In preferred embodiments, the native disc material is removed either before or simultaneously with the HCF addition. Preferably, the volume of native material removed is at least 50% of that of the volume of HCF added, more preferably at least 75%.

In other embodiments, the HCF material is first added to the disc, and then excess fluid within the disc is removed to lower the pressure within the HCF-containing disc.

In some embodiments, the HCF added to the nucleus pulposus may undesirably diffuse widely throughout the nucleus pulposus to contact healthy portions of the annulus fibrosus. Subsequent application of energy to such an HCF-augmented disc may lead to undesired heating of healthy portions of the nucleus pulposus and the annulus fibrosus.

The present inventors believe that providing an HCF that has a viscosity higher than that of isotonic saline will mitigate the dilution problem associated with ITS.

Preferably, the HCF has a viscosity at least 5 times greater than that of ITS, more preferably at least 10 times. In preferred embodiments, this high viscosity HCF is provided as a viscous gel. When a viscous gel is selected, it preferably comprises fibrin, more preferably autologous fibrin. Preferably, the high viscosity HCF is deposited substantially adjacent and/or within the targeted fissure so as to mitigate the heating of adjacent healthy tissue.

In some embodiments, the HCF further comprises a contrast agent that allows the surgeon to visualize the movement of the HCF under fluroscopy. Preferably, the contrast agent comprises a radio-opaque material. Preferably, the radio-opaque material comprises a species selected from the group consisting of barium, zirconium, tungsten and tantalum, and mixtures thereof. More preferably, the radio-opaque material comprises barium.

Preferred embodiments of the present invention are directed generally to welding fissures in collagen tissue by coagulating a target tissue immediately surrounding the fissure. Preferably, the target collagen tissue is the annulus fibrosus of an intervertebral disc. More preferably, the target tissue is the posterior portion of the annulus fibrosus. However, in other embodiments, the target tissue is an anterior or a lateral portion of the annulus fibrosus.

In some embodiments, a fissure in the annular wall begins at the inner wall of the annulus, extends outward towards the outer wall of the annulus fibrosus, and terminates within the annulus. This is called an "inner fissure". In these cases, the HCF is preferably deposited within either the nucleus pulposus of the disc (preferably at the mouth of the fissure) or within the inner fissure, or both.

In some embodiments, the fissure begins at the outer wall of the annulus, extends inward and terminates within the annulus. This is called an "outer fissure". In these cases, the HCF is preferably deposited within the outer fissure, or upon the outer wall of the annulus fibrosus (preferably at the mouth of the fissure), or both.

In some embodiments, the fissured portion of the annular wall extends from the inner wall to the outer wall of the annulus. This is called a "through-fissure". In these cases, the HCF is preferably deposited within the through-fissure, within the nucleus pulposus (preferably at the mouth of the fissure) or upon the outer wall of the annulus fibrosus.

In one particular through-fissure embodiment, the through-fissure is caused by a discectomy, wherein a probe surgically punctures the annulus fibrosus in order to allow a tool into the nucleus pulposus. Since the diameter of the catheter of the present invention can be much smaller than the probe used in a discectomy, the present invention can be used to reduce or eliminate the puncture hole of a discectomy.

In some preferred embodiments, the present invention may be practiced upon an annulus having a plurality of torn plies. Now referring to FIG. 3, an annulus 31 having torn pliesis characterized by a plurality of laterally-extending tears 35 between the plies 33 which make up the wall of the annulus fibrosus. These tears are often associated with the earliest stages of disc degeneration. In addition, there may be pain that could be associated with local instability and/or incompetency of the annulus, leading to hypermobility. In some embodiments, intra-annular deposition of the HCF and intra-annular placement of the electrodes may be required.

In some preferred embodiments, the present invention may be practiced upon a torn annulus. Now referring to FIG. 4, a torn annulus is characterized by a radially extending hairline break 41 in the wall 43 of the annulus fibrosus 45 and is often caused by a sudden movement. In this instance, pain is caused by the sensitization of nociceptors present (not shown) in the annulus fibrosus in the vicinity of the tear.

In some preferred embodiments, the present invention may be practiced upon a herniated disc. Now referring to FIG. 5, a herniated disc is characterized by a radially extending deformation 51 in the inner wall 53 of the annulus fibrosus 55 and is often caused by the nucleus pulposus 57 pressing upon a weakened portion of the annulus wall. The weakened portion often takes a substantially hemispherical shape having a diameter of between about 5 and 15 mm. In this instance, pain is caused by the sensitization of nociceptors present in the annulus fibrosus in the vicinity of the herniation, or by pressure or inflammation imparted by the distended outer wall upon a nerve root of the spinal cord.

In some preferred embodiments, the present invention may be practiced upon a ruptured disc. Now referring to FIG. 6, a ruptured disc is characterized by a complete tear 61 or "through hole" in the wall 63 of the annulus fibrosus 65 providing a pathway for the nucleus pulposus material to exit the disc. In this instance, pain is caused by pressure or inflammation imparted by the outer wall or extruded nucleus pulposus upon the adjacent nerve root. In addition, the rupture may cause future extravasation of the nucleus pulposus.

Generally, the methods of the present invention raise the temperature of the target collagen tissue to between about 42° C. and about 90° C. It is believed that temperatures in this range have the effect of denervating or coagulating the collagen tissue. Preferably, the methods of the present invention raise the temperature of the target collagen tissue to between about 60° C. and about 80° C., as in this range coagulation occurs. More preferably, the methods of the present invention raise the temperature of the target collagen tissue to between about 60° C. and about 70° C., as this range both shrinks and reforms the affected collagen to produce a new collagen structure having a reasonably strong state.

In other embodiments, the methods of the present invention raise the temperature of the target collagen tissue to between about 45° C. and about 60° C. It is believed that temperatures in this range have the effect of denervating the nociceptors within the collagen tissue.

It is further believed that the methods of the present invention can produce a temperature of between 45° C. and 90° C. in no more than eight (8) minutes. Preferably, the methods of the present invention can produce a temperature of between 60° C. and 70° C. in no more than four (4) minutes. When the target temperature is achieved in no more than two (2) minutes, the feedback controls associated with the system will more quickly lower the power level of the apparatus to maintain the target temperature at a steady state.

In preferred embodiments of the present invention, the ECF is first directed to the target tissue, and then a current is passed through the ECF to resistively heat the ECF. This procedure is superior to that of Hovda, which disclosed first resistively heating the ECF, and then directing it to the target tissue, in that heat in the fluid is not lost during transport to the target tissue.

Therefore, in accordance with the present invention, there is provided a method of therapeutically treating a target tissue within an intervertebral disc, comprising the sequential steps of:

a) directing an electrically conductive fluid to the target tissue, and
b) passing a current through the conductive fluid to resistively heat the conductive fluid.

Generally, the apparatus of the present invention comprises an energy delivery device suitable for delivering energy to the intervertebral disc. Preferably, the energy delivery device provides an electrical current through the HCF. The device may supply the current directly in contact with the target tissue or through induction. When direct contact is selected, the power source supplying the current is preferably radiofrequency (RF). Preferably, the RF energy is provided at a frequency of between 100 kHz and 1000 kHz. Below about 100 kHz, the RF energy may have little effect upon the target tissue. Above 1000 kHz, the system may be quickly overheated. More preferably, the RF energy is provided at a frequency of between 400 kHz and about 600 kHz.

When providing an RF current through the HCF is desired, in some embodiments, the device comprises an active electrode and a return electrode, and the direct current runs between the electrodes. In some embodiments, such a device is bipolar. Bipolar devices disclosed in U.S. Pat. No. 6,264,650 ("Hovda"), the specification of which relating to bipolar devices is incorporated by references, may be used.

In general, the spacing of the bipolar electrodes changes the depth to which the current flows. When the electrodes are spaced far apart, the current only penetrates into the tissue near the electrodes. If the electrodes are spaced moderately apart, the current penetrates relatively deep into the tissue. When the electrodes are more closely spaced, the current penetrates to a relatively shallow depth into the tissue. In preferred embodiments of the present invention, the active and return electrodes are spaced between 2 mm and 6 mm apart. When the spacing is less than 1 mm, the current penetration depth may be insufficient. When the spacing is more than 8 mm, the heating profile will become significantly non-uniform, with the majority of the heating occurring substantially in the vicinity of the electrodes.

In some preferred embodiments, the electrode spacing is between 5.1 mm and 15 mm. Such spacing can be used to advantageously treat bulging discs.

Therefore, in accordance with the present invention, there is provided an instrument for therapeutically treating an intervertebral disc having an annulus fibrosus, comprising an active electrode and a return electrode, wherein the active and return electrodes are separated to define a spacing of between 5.1 mm and 15 mm.

In general, the surface area of the electrodes changes the density of the RF current. At a constant power level, when the surface area of an electrode is relatively large, the current density is low, and when the surface area of an electrode is relatively small, the current density is relatively high. In preferred embodiments of the present invention, the active and return electrode each have a surface area of between 3 mm$^2$ and 45 mm$^2$. This range of surface area allows for sizes that can be inserted into the disc through a conventional catheter. In some embodiments, the electrode has a length of between 2 mm and 5 mm, and is preferably substantially arcuate in shape. In some embodiments, the electrode has a cylindrical or hemi-cylindrical shape having a diameter of between 0.5 and 3.0 mm.

In some embodiments of the present invention, the surface area of the return electrode is between 2 and 5 times larger than the surface area of the active electrode. When this ratio of surface areas is selected, the tissue adjacent the active electrode will experience a relatively high current density as compared to the tissue adjacent the return electrode, and so will preferentially heat. The preferential heating may be useful in at least two situations. First, if the active electrode is situated near the mouth of a fissure, the energy can be preferentially deposited near the mouth and seal the mouth. Second, if the return electrode is disposed adjacent the outer wall of the annulus fibrosus, its proximity to the spinal cord may be of concern, and reducing heat near the spinal cord may be desirable.

In some embodiments, the surface area of the active electrode is greater than the surface area of the fissure. In this condition, the current will increase in density as it moves from the nucleus pulposus into the fissure.

Figure 7:
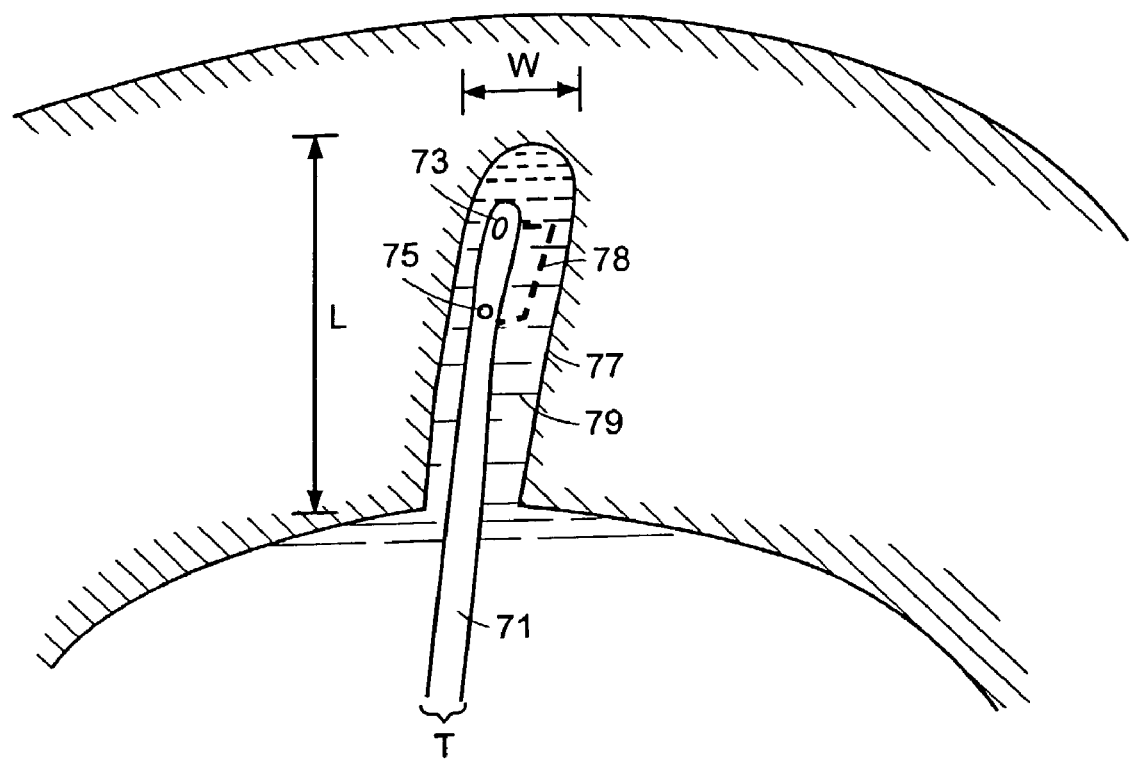
FIG. 7 discloses an embodiment wherein the electrodes are disposed within the fissure and produce current substantially only within the ECF.

In some embodiments, the width of the distal end of the catheter is sized to be passable within the width of the fissure. In this condition, at least one electrode on the catheter can be positioned within the fissure. Now referring to FIG. 7, there is provided a bipolar device wherein the distal end 71 of the catheter is sufficiently thin so that the first 73 and second 75 electrodes thereon can be placed within the fissure 77. Because each electrode is within the fissure, current 78 flowing from the active electrode to the return electrode should remain within the HCF 79 located within the fissure.

Preferably, the instrument is further sized so that the space between the electrodes is between 50% and 125% of the length L of the fissure, more preferably between 75% and 100%. This allows substantially the entire fissure to be treated.

Since the catheter of this embodiment must fit within the fissure, and the width of a fissure within the annulus fibrosus may range from hairline to about 2 mm, the thickness T of the distal end of the catheter should be less than about 1.75 mm. However, if the thickness of the distal end of the catheter is less than about 0.75 mm, the catheter becomes difficult to steer or push. Therefore, in some embodiments of the present invention, the thickness of the distal end of the catheter is preferably between 0.75 mm and 2 mm, more preferably between 0.75 mm and 1 mm.

Since the electrodes of this embodiment must also fit within the fissure, and length L of a fissure within the annulus fibrosus ranges from hairline to about 10 mm, the electrode spacing should be less than about 10 mm. However, if the electrode spacing becomes less than 1 mm, shorting may occur. Therefore, in some embodiments of the present invention, the spacing of the electrodes should be between 2 mm and 10 mm, more preferably between 3 mm and 5 mm.

Figure 8:
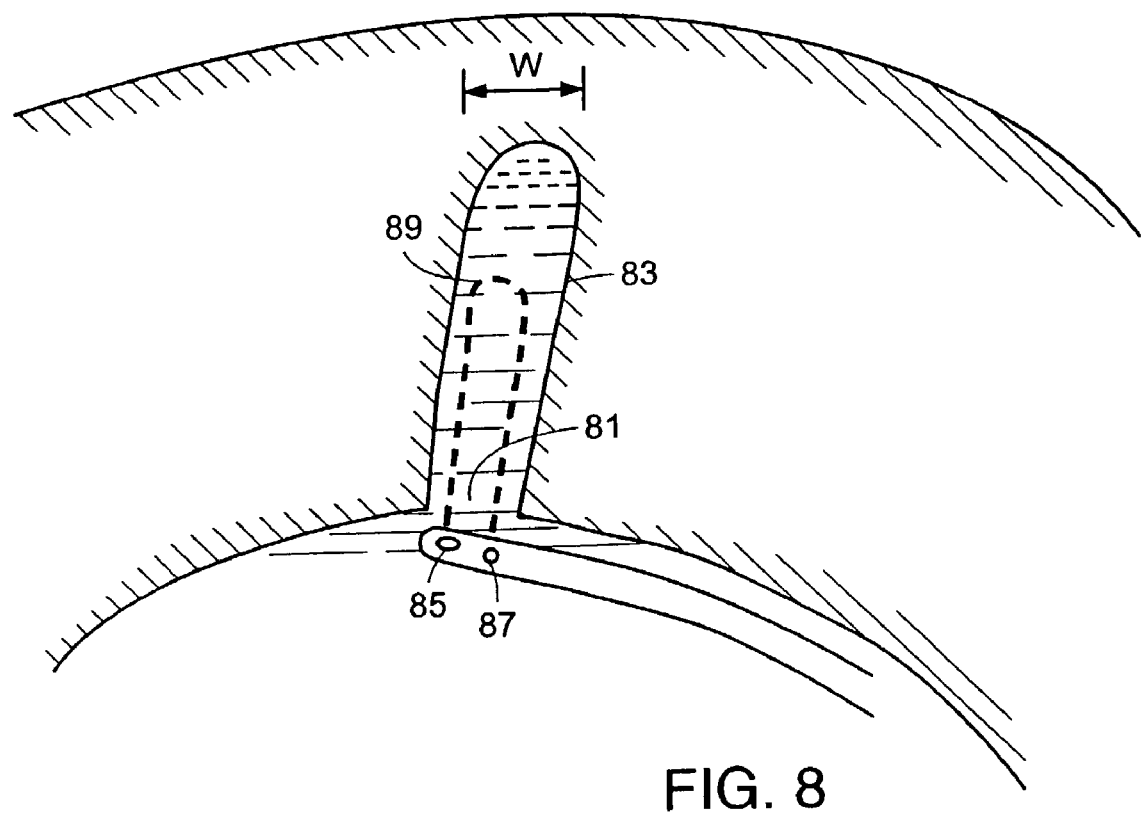
FIG. 8 discloses an embodiment wherein the electrodes are disposed at the mouth of the fissure and between the sidewalls of the fissure to produce current substantially only within the ECF.

In some bipolar embodiments, the spacing of the electrodes is less than the width of the fissure. In this condition, the first 85 and second 87 electrodes can be positioned substantially directly in front of the mouth 81 of the fissure 83. This is advantageous because the current path produced thereby will be essentially through the HCF. Because the penetration depth of current 89 of a bipolar electrode is greater in high conductivity media, the penetration depth of the current will be maximized. Now referring to FIG. 8, there is provided a bipolar electrode wherein the spacing of the electrodes is less than the width of the fissure. Because the spacing of the electrodes is less than the width W of the fissure, the current will flow essentially only within the high conductivity HCF disposed within the fissure. Accordingly, current will selectively flow only within the fissure, and current penetration will be maximized.

Therefore, in accordance with the present invention, there is provided method of therapeutically treating a fissure in an annulus fibrosus of an intervertebral disc, the fissure having a mouth and a width, comprising the steps of:
a) providing a bipolar device having an active electrode and a return electrode, the electrodes being spaced at a first distance, the first distance being less than than the width of the fissure, and
b) positioning the device adjacent the mouth of the fissure,
c) applying a sufficiently high frequency voltage difference between the first and second electrode to generate a current therebetween flowing substantially only within the fissure and preferentially heating the HCF to therapeutically treat the tissue adjacent the fissure.

Since the electrode spacing of this embodiment must be less than the width of the fissure, and width of a fissure within the annulus fibrosus may range from hairline to about 5 mm, the electrode spacing should be less than about 5 mm. However, if the thickness of the distal end of the catheter is less than about 0.75 mm, it becomes difficult to steer or push. Therefore, in some embodiments of the present invention, the thickness of the distal end of the catheter is preferably between 0.75 mm and 2 mm, more preferably between 0.75 and 1 mm.

Figure 9:
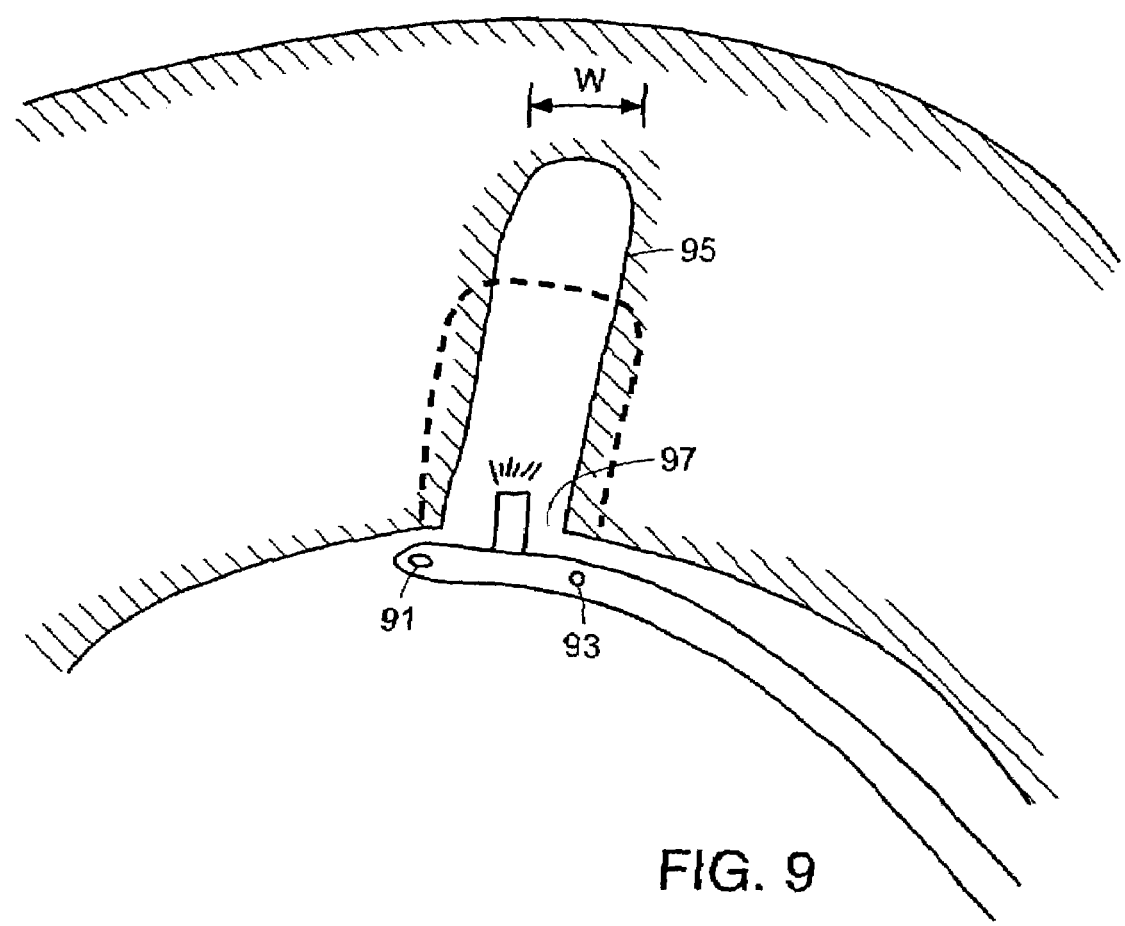
FIG. 9 discloses an embodiment wherein the electrodes are well spaced to provide deep penetration of the current into the annulus.

Now referring to FIG. 9, in some bipolar embodiments, the spacing of the first 91 and second 93 electrodes is greater than the width W of the fissure 95. In this condition, each electrode can be positioned substantially on either side of the mouth 97 of the fissure. The large spacing of the electrodes is advantageous because the current path produced by well-spaced electrodes will more deeply penetrate the tissue than less-well spaced electrodes (i.e., if the spacing were less than the fissure width. Because the penetration depth of current of a bipolar electrode is greater in well-spaced electrodes, the penetration depth of the current will be maximized. In some embodiments using a bipolar electrode, the spacing of the electrodes is greater than the width of the fissure. In this condition, the electrodes are placed either in contact with the opposing sidewalls of the fissure or in sufficiently close proximity thereto so that current flow first enters the tissue and then crosses through the HCF-filled fissure in a substantially normal direction. Since the current flows through both the tissue and the HCF-filled fissure, and the tissue has a relatively low conductivity tissue, the tissue will be heated directly by the current, and not by the heated HCF. Therefore, this configuration is advantageous because the heating is localized.

Therefore, in accordance with the present invention, there is provided method of therapeutically treating a fissure in an annulus fibrosus of an intervertebral disc, the fissure having a mouth and a width, and defining first and second adjacent collagen tissue regions, comprising the steps of:
a) providing an energy device having an active electrode and a return electrode, the electrodes being spaced at a first distance, the first distance being greater than the width of the fissure, and
b) positioning the device at the mouth of the fissure so that the active electrode is adjacent the first sidewall of the fissure and the second electrode is adjacent the second sidewall of the fissure,
c) applying a sufficiently high frequency voltage difference between the active and return electrodes to generate a current therebetween flowing from the first sidewall through the width of the fissure and into second sidewall and resistively heat the first and second adjacent collagen tissue regions to therapeutically treat the tissue regions.

In some embodiments, the current penetration is such that only the tissue substantially adjacent the mouth of the fissure is coagulated. This promotes energy efficiency. In some embodiments, the probe may be sectored so that the active electrode face of the probe faces the fissure.

Figure 10:
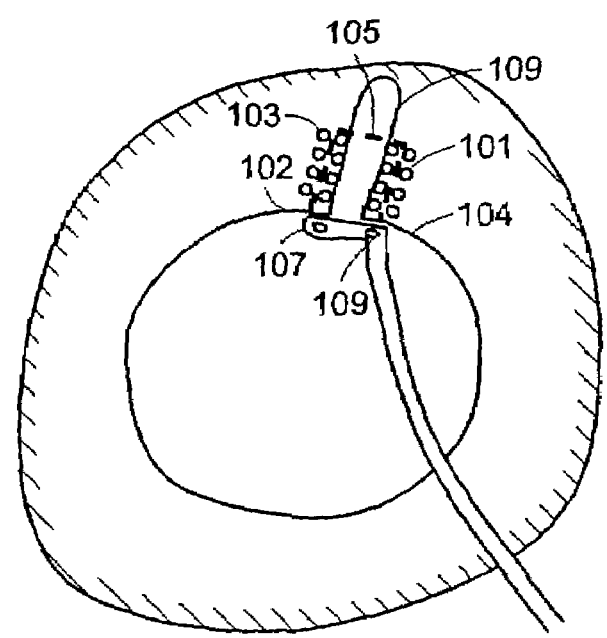
FIG. 10 discloses an embodiment wherein the closely adjacent collagen tissue regions are porous.

Now referring to FIG. 10, in some embodiments, the closely adjacent collagen tissue regions 101 have an open porosity 103 that is connected to the fissure. In this case, the HCF added to the fissure also permeates the open porosity of these regions to increase the electrical conductivity of the closely adjacent collagen tissue regions. In such a case, the electrodes may be spaced so that current 105 flows from the first electrode 107 to first sidewall 102 through the HCF-filled portions of the first closely adjacent collagen tissue region, through the width of the HCF-filled fissure 109, through the HCF-filled portions of the second closely adjacent collagen tissue region 101 to the second sidewall 104 and to the second electrode. This embodiment provides a current path that is not only a highly preferential (as each part of the path can flow through an HCF-filled region), but also a path which can accept a high level of power (since the HCF-filled regions can accept a higher level of power).

Therefore, in accordance with the present invention, there is provided method of therapeutically treating an intervertebal disc having an annulus fibrosus having a fissure defining first and second adjacent collagen tissue regions having open porosity, comprising the steps of:
a) adding a hyperconductive fluid to the fissure and the open porosity of the adjacent collagen tissue regions,
b) positioning a first electrode adjacent to the hyperconductive fluid,
c) applying a sufficiently high frequency voltage difference between the first electrode and a second electrode to generate an current flowing substantially only through the fissure and the open porosity of the adjacent collagen tissue regions.

In some embodiments, the catheter further comprises a fluid outlet, wherein the outlet is disposed between the active and return electrodes.

Figure 3:
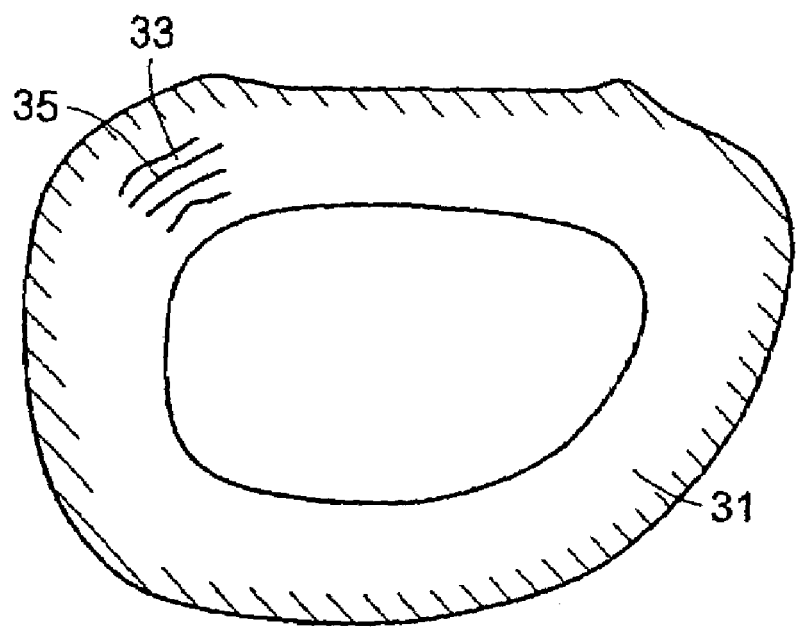
FIGS. 3-6 are images of degenerated discs respectively having delamination of annular layers (or "broken plies"), a torn annulus, a herniation, and a ruptured annulus.
Figure 11:
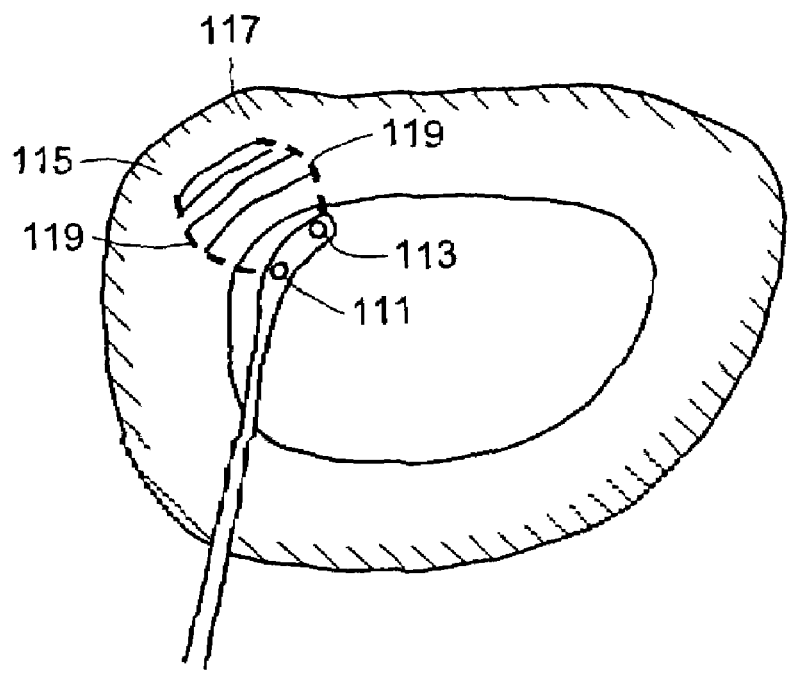
FIG. 11 discloses an embodiment wherein a device having well spaced electrodes therapeutically treats delamination of annular layers (or "broken plies").

In some preferred embodiments, the device of FIG. 9 having well spaced electrodes is advantageously used in treating the broken plies of FIG. 3. Now referring to FIG. 11, when the device of FIG. 9 is selected, the spacing of the first 111 and second 113 electrodes is selected so that the first electrodes and second electrodes essentially straddle the first 115 and second 117 ends of the tear. Once HCF is infused into the fissures through intra-annular injection, the current 119 will flow from the first electrode to the first end of the tear, through the HCF to the second end of the tear, and to the second electrode. In addition, because the HCF is fairly localized, only the site in need of treatment is affected by the current, thereby preserving healthy tissue. Since the effect of broken plies is a weakening of the annulus which may lead to the more serious degeneration, it may be desirable to weld the broken plies by providing sufficient current to heat the closely adjacent tissue regions to at least 60° C. so that the local tissue coagulates. However, if these tears are simply a source of pain, in some embodiments, additionally, the treatment need only heat the localized area to between about 45° C. and 60° C., thereby minimizing damage to the effected tissue. Since the length of the broken plies is often between 5 mm and 15 mm, in preferred embodiments, the spacing of the electrodes is between 5.1 mm and 15 mm, more preferably between 7 mm and 10 mm. However, if the electrode lengths exceed about 5 mm, then the spacing therebetween should not be more than about 10 mm.

Figure 5:
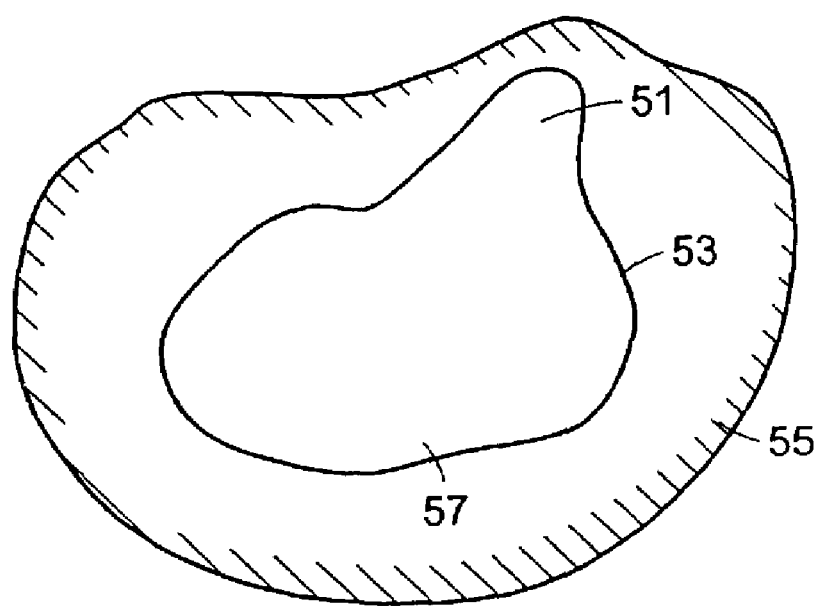
Figure 12:
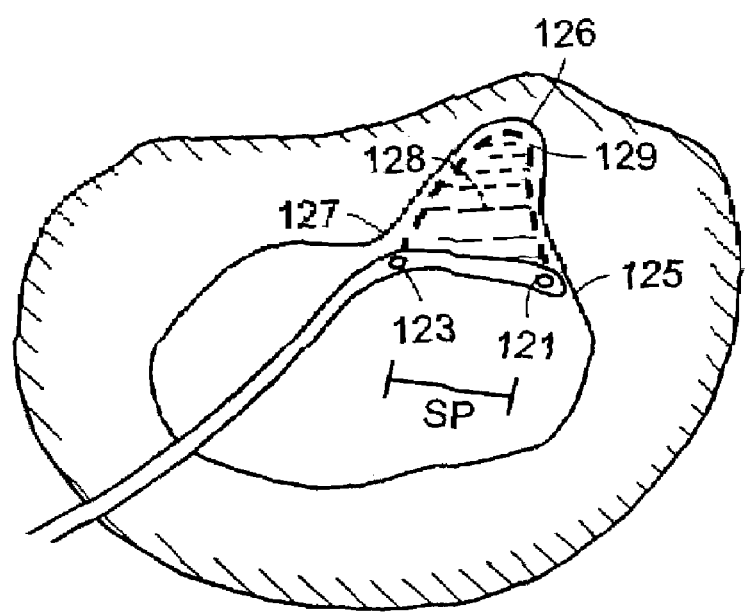
FIG. 12 discloses an embodiment wherein a device having well spaced electrodes therapeutically treats a contained herniation.

In some preferred embodiments, the device of FIG. 9 having well spaced electrodes is advantageously used in treating the herniated disc of FIG. 5. Now referring to FIG. 12, when the device of FIG. 9 is selected, the spacing of the electrodes is selected so that the first electrode 121 and second electrode 123 essentially straddle the first 125 and second 127 ends of the herniation. Once HCF 128 is infused into the herniation, the current 129 will flow from the first electrode to the first end of the herniation, along the periphery 126 of the herniation through the HCF to the second end of the herniation, and return to the second electrode. In addition, the current flows only adjacent the site in need of treatment, thereby preserving healthy tissue. Preferably, since the shape of the herniation may be causing pressure upon the nerve root, it may be desirable to coagulate the collagen fibers forming the herniation by providing sufficient current to heat the tissue regions closely adjacent the herniation to at least 60° C. so that the local tissue coagulates. However, if the herniation is simply a source of pain due to local nociceptors, in some embodiments, the treatment need only heat the localized area to between about 45° C. and 60° C., thereby minimizing damage to the effected tissue. Since the diameter of the herniation is often between 5 mm and 15 mm, in preferred embodiments, the spacing SP of the electrodes is between 5.1 mm and 15 mm, more preferably between 7 mm and 10 mm. However, if the electrode lengths exceed about 5 mm, then the spacing therebetween should not be more than about 10 mm.

In some bipolar embodiments, a first electrode is disposed adjacent the outer wall. In this condition, the first electrode can be positioned on the outer wall substantially directly in line with the axis of the fissure. This is advantageous because the current path produced thereby will essentially flow straight through the HCF-containing fissure.

Figure 13:
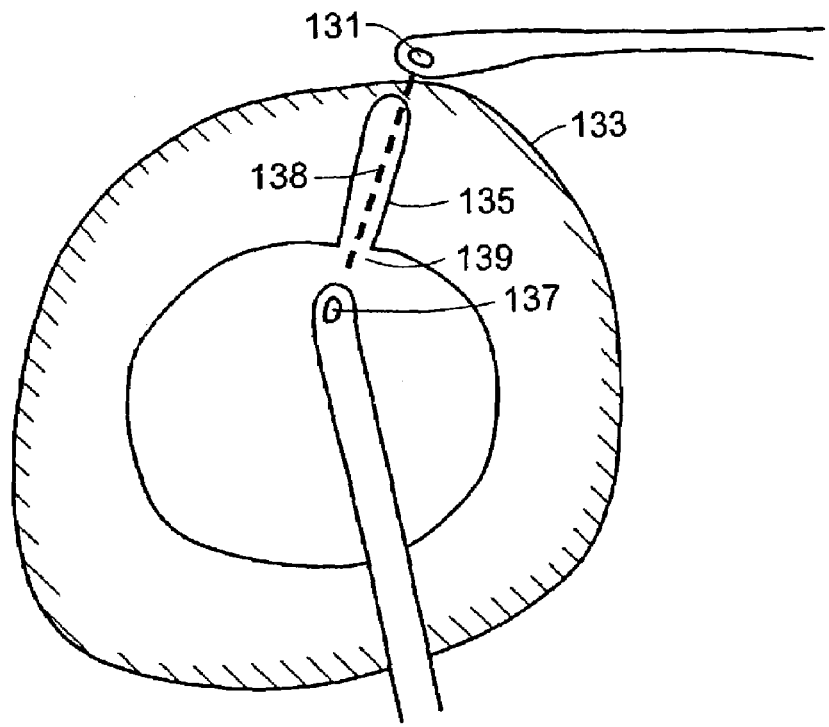
FIG. 13 discloses an embodiment wherein a first electrode is disposed at the mouth of the fissure, and a second electrode is disposed adjacent the outer wall of the fissure.

Now referring to FIG. 13, the first electrode 131 is positioned on the outer wall 133 substantially directly in line with the axis of the fissure 135, while the second electrode 137 is positioned substantially at the mouth 139 of the fissure. The current path 138 essentially follows the axis of the fissure. Since the high conductivity of the HCF allows the fissure to accept more energy than a lower conductivity region, the HCF will heat quickly.

Therefore, in accordance with the present invention, there is provided a method of therapeutically treating a fissure in an annulus fibrosus of an intervertebral disc, the fissure having an axis, and defining first and second adjacent collagen tissue regions comprising the steps of:
a) providing an energy electrode having a first electrode and a second electrode,
b) positioning the first electrode within the disc,
c) positioning the second electrode adjacent the outer wall,
d) applying a sufficiently high frequency voltage difference between the first and second electrode to generate a current therebetween flowing substantially along the fissure axis to preferentially resistively heat the HCF and therapeutically treat the adjacent collagen tissue regions.

In some embodiments, the first electrode disposed adjacent the outer wall is positioned within the annular wall. In preferred embodiments, however, the first electrode contacts the outer wall.

Therefore, in accordance with the present invention, there is provided a method of therapeutically treating an intervertebral disc having an annulus fibrosus having an outer wall, comprising the steps of:
a) inserting a first electrode into the disc, and
b) placing a second electrode adjacent the outside wall of the annulus fibrosus, and
c) applying a sufficiently high frequency voltage difference between the first and second electrode to generate a current therebetween.

Also in accordance with the present invention, there is provided an instrument for therapeutically treating an intervertebral disc having an annulus fibrosus, comprising:
a) a first catheter adapted to penetrate the annulus fibrosus and having a first electrode, and
b) a second catheter adapted to contact an outer wall of the annulus fibrosus and having a second electrode.

In some embodiments, the second electrode is placed in the inner portion of the nucleus pulposus. This allows multiple fissures disposed about the entire circumference of the nucleus pulposus to be heated simultaneously.

In some embodiments, the second electrode is placed in the outer portion of the nucleus pulposus. This allows multiple fissures in a given region to be heated simultaneously, without expending energy in the non-fissured regions.

In some embodiments, as in FIG. 13, the second electrode is placed substantially adjacent the mouth of the fissure. This allows the current path to travel essentially only in the fissure without experiencing heat loss in the nucleus pulposus.

In some preferred embodiments wherein the second electrode is positioned substantially at the mouth of a fissure, the second electrode is first positioned adjacent a first fissure to therapeutically treat substantially the first fissure, and then positioned adjacent a second fissure to therapeutically treat substantially the second fissure.

This embodiment is advantageous because it provides precise, selective treatment of the target fissure site and does so in an energy efficient manner, thereby avoiding damage to healthy adjacent tissue.

Figure 4:
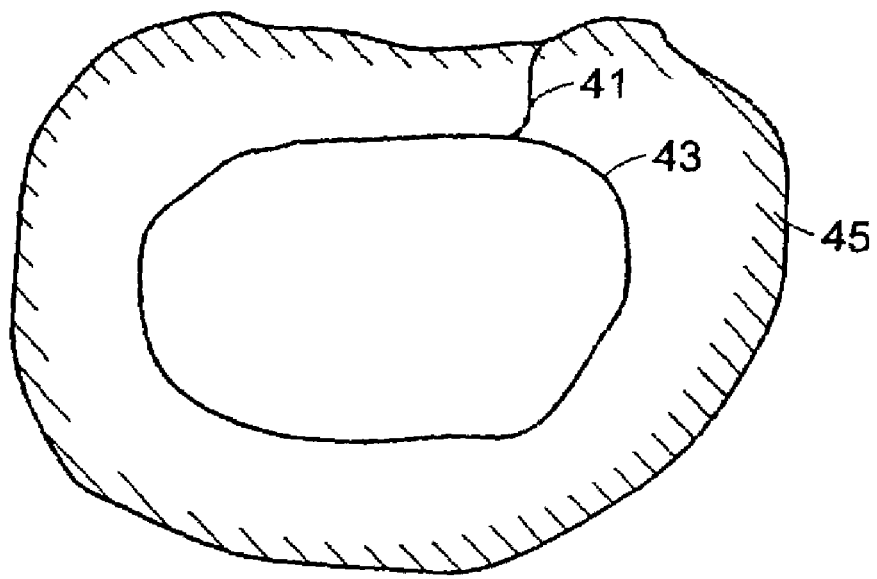
Figure 14:
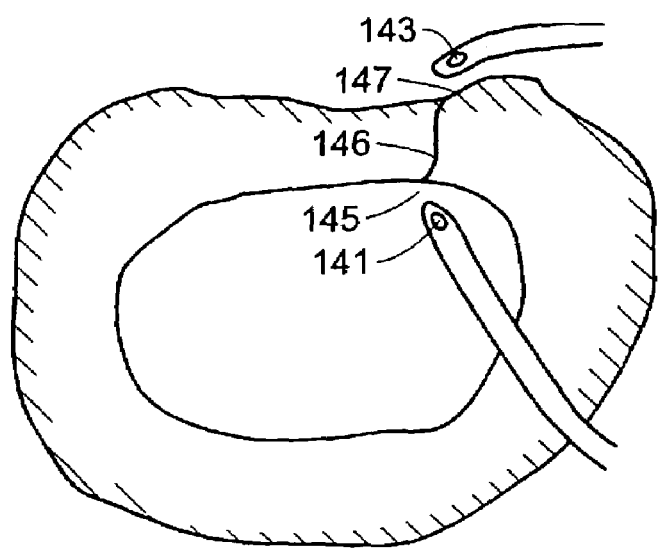
FIGS. 14 and 15 disclose embodiments wherein a device having two catheters therapeutically respectively treats a torn annulus and a ruptured annulus.

In some preferred embodiments, the device of FIG. 13 is advantageously used in treating the torn annulus of FIG. 4. Now referring to FIG. 14, when this device is positioned so that the first 141 and second 143 electrodes are adjacent to the first 145 and second 147 ends of the tear 146 (preferably, each electrode contacting the annulus fibrosus), and HCF is infused into the fissure, the current will flow through the HCF substantially along the path of the tear. Because the HCF is fairly localized, only the site in need of treatment is affected by the current, thereby preserving healthy tissue. In addition, since the source of pain in the torn annulus may be simply the nociceptors contained within the annulus fibrosus, in preferred embodiments, the treatment need only heat the localized area to between about 45° C. and 60° C., thereby minimizing damage to the effected tissue.

Figure 6:
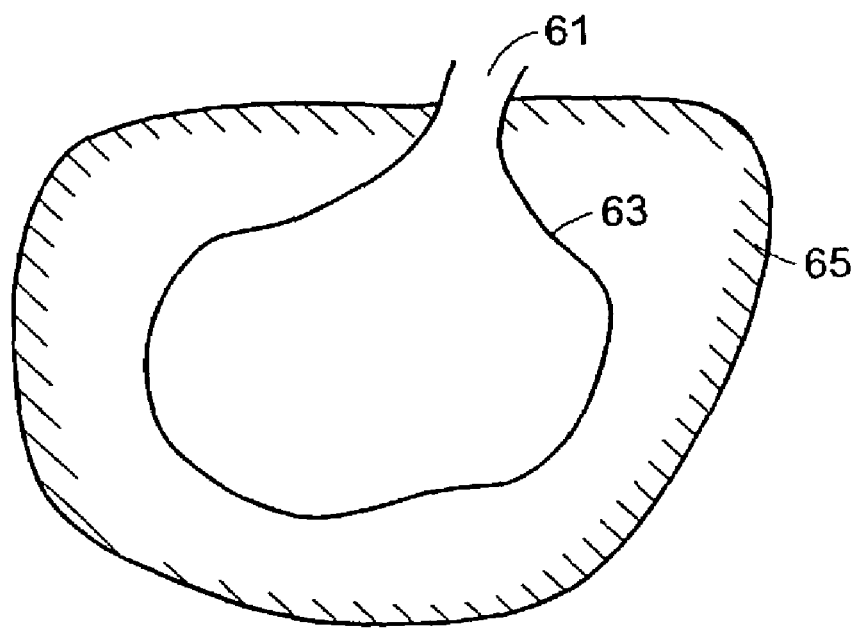
Figure 15:
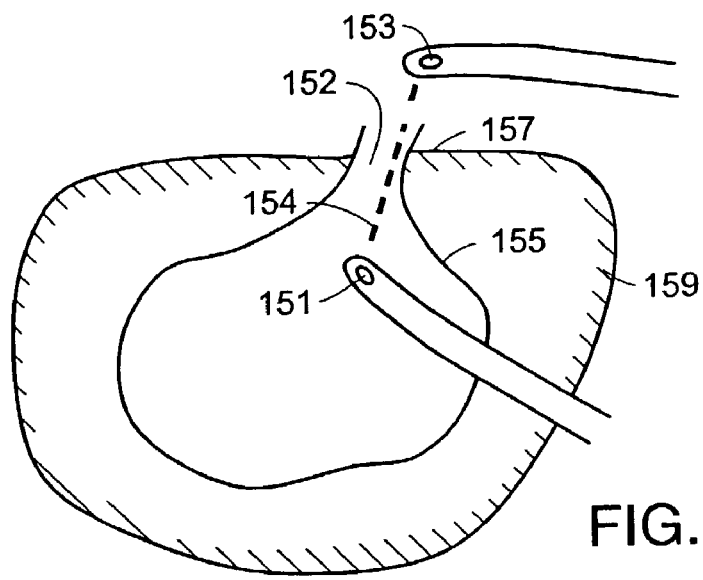

In some preferred embodiments, the device of FIG. 13 is advantageously used in treating the ruptured disc of FIG. 6. Now referring to FIG. 15, when this device is positioned so that first 151 and second 153 electrodes are adjacent to both the inner 155 and outer 157 walls of the annulus fibrosus 159 and adjacent the through hole, and HCF is infused into the through hole 152, the current 154 will flow through the HCF substantially along the path of the through hole. In this case, the use of a viscous gel containing the HCF will help maintain the HCF at the site of treatment and prevent its exiting the disc. Because the HCF is fairly localized only the site in need of treatment is affected by the current, thereby preserving healthy tissue. In some embodiments respecting the treatment of a ruptured disc, the HCF comprises a viscous gel that will remain substantially in place.

In some embodiments, the instrument can include sesquipolar electrodes, preferably having an active electrode and a pair of return electrodes. The sesquipolar configuration of the instrument allows two tissue regions to be heated at the same time.

In some embodiments, the two tissue regions are associated with the same fissure. Now referring to FIG. 16, sesquipolar electrode has an active electrode 161 sized to fit within the fissure and first 163 and second 165 return electrodes spaced from the active electrode to be disposed within the tissue adjacent the fissure. When the instrument is activated, a first current flows from the active electrode to the first return electrode, and a second current flows from the active electrode to the second return electrode. Preferably, these electrodes are spaced between 3 mm and 5 mm apart.

Therefore, in accordance with the present invention, there is provided a method of therapeutically treating a fissure in an annulus fibrosus of an intervertebral disc, the fissure having a width and defining first and second tissue adjacent collagen regions, comprising the steps of:

a) providing a bipolar electrode having an active electrode and a first and a second return electrode, and
b) positioning the active electrode within the fissure adjacent the mouth of the fissure,
c) positioning the first and second return electrodes within the first and second respective tissue regions, and
d) applying a sufficiently high frequency voltage difference between i) the active electrode and ii) each of the first and second return electrodes to generate a first and a second current therebetween flowing from the fissure through its width and into the first and second tissue regions to therapeutically treat the tissue adjacent the fissure.

Figure 16:
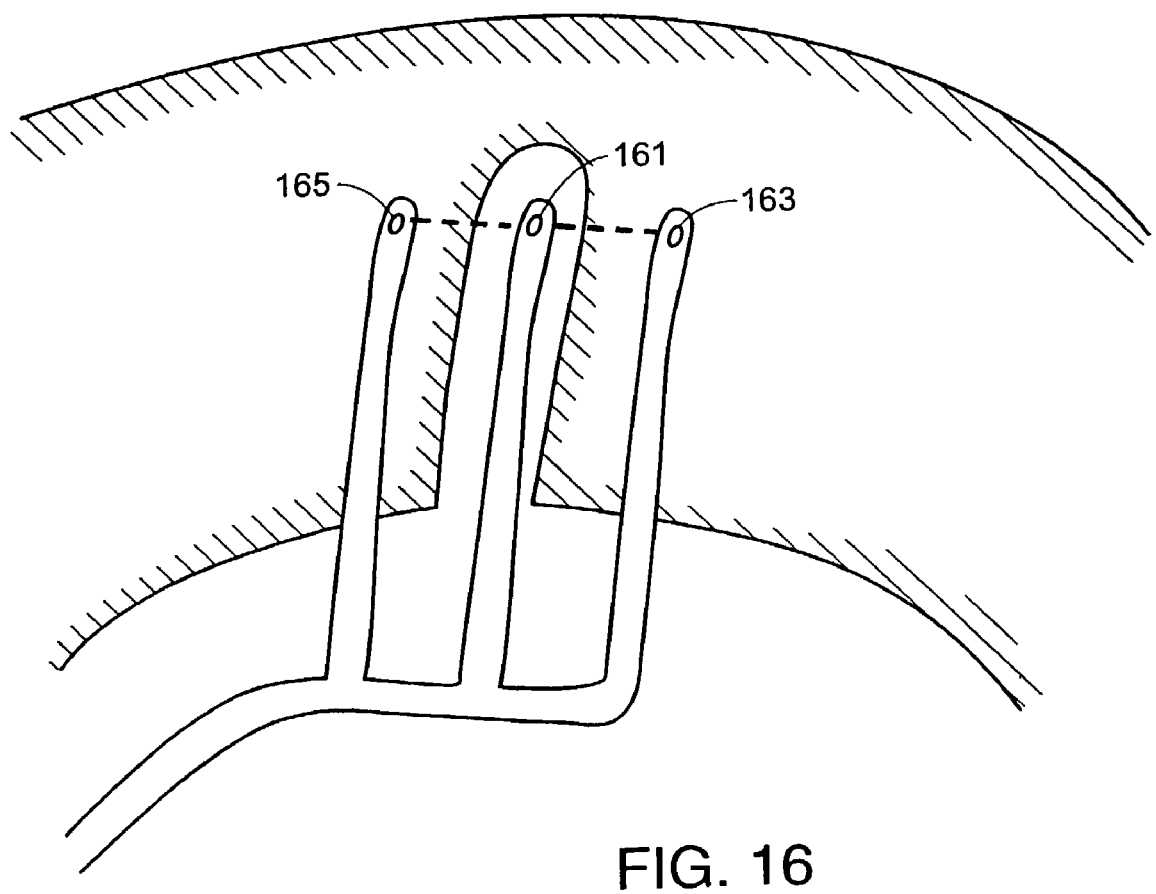
FIG. 16 discloses a sesquipolar device wherein the active electrode is disposed within the fissure and the return electrodes are disposed in the tissue regions closely adjacent the fissure.
Figure 17:
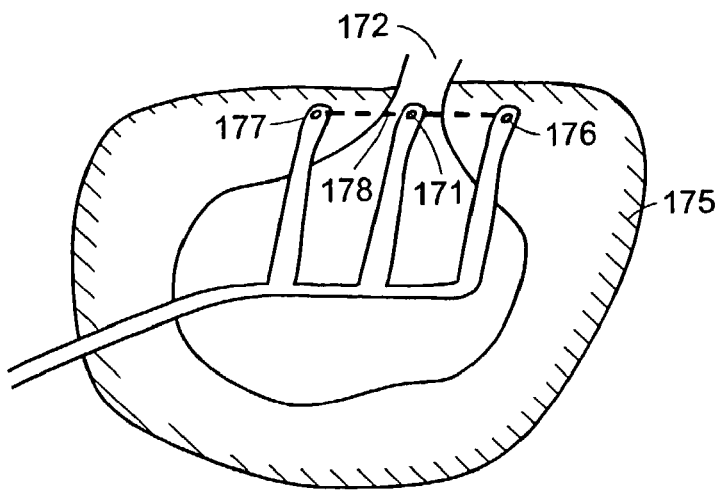
FIG. 17 discloses an embodiment wherein a sesquipolar device therapeutically respectively treats a ruptured annulus.

In other preferred embodiments, the device of FIG. 16 is advantageously used in treating the ruptured disc of FIG. 6. Now referring to FIG. 17, when this device is positioned so that the active electrode 171 is initially positioned in the through hole 172 in an outer portion 173 of the annulus fibrosus 175, and the first 176 and second 177 return electrodes are disposed within the annulus fibrosus at a similar depth. Activation of the device causes current 178 to flow from the active electrode laterally to each return electrode. In this case, the use of a viscous gel containing the HCF will help maintain the HCF at the site of treatment and prevent its exiting the disc. Because the HCF is fairly localized only the site in need of treatment is affected by the current, thereby preserving healthy tissue.

In some embodiments related to the treatment of a ruptured disc, the center active electrode further comprises a fluid outlet that can deliver the HCF to the treatment site.

In preferred embodiments, the adjacent tissue regions in the outer portion of the annulus wall are first coagulated (thereby effectively closing the opening forming the through hole), and the device is gradually withdrawn as progressively interior portions of the closely adjacent tissue regions coagulate, thereby insuring that the closing of the through hole keeps the HCF within the disc In other embodiments, the device comprises a monopolar device. Monopolar devices disclosed in U.S. Pat. No. 5,433, 739 ("Sluitjer"), the specification of which relating to monopolar devices is incorporated by reference, may be used.

Figure 18:
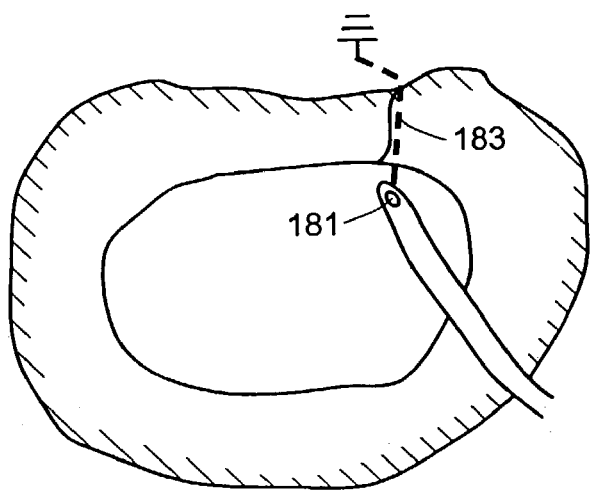
FIG. 18 discloses an embodiment wherein a monopolar instrument is disposed substantially adjacent the mouth of a fissure.

Now referring to FIG. 18, in some embodiments having a single fissure to be treated, the monopolar electrode 181 is placed substantially adjacent the inside of the fissure 183. This configuration may force the current path to travel essentially only in the fissure without experiencing heat loss in the nucleus pulposus. Preferably, the HCF of this embodiment is disposed substantially only within the fissure.

In other embodiments using a monopolar electrode, the active electrode is first positioned adjacent a first fissure to therapeutically treat substantially the first fissure, and then positioned adjacent a second fissure to therapeutically treat substantially the second fissure.

Figure 19:
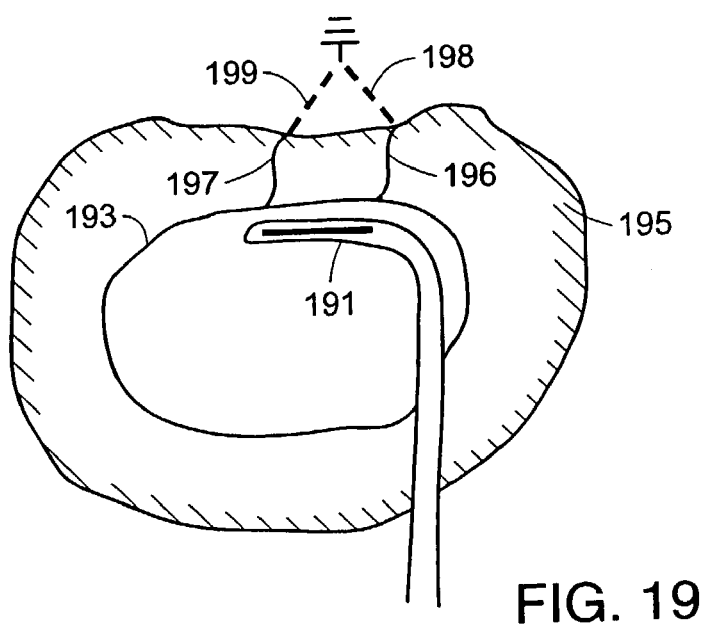
FIG. 19 discloses an embodiment wherein a monopolar instrument is disposed within the outer portion of the nucleus pulposus.

Now referring to FIG. 19, in some embodiments having more than one fissure to be treated, the monopolar electrode 191 has a relatively long length and is positioned alongside the inner wall 193 of the annulus 195 so as to be in proximity to the mouths of each fissure 196, 197 to be treated. When the instrument is activated, a first portion 198 of the current flows from the active electrode through the first fissure to the ground, and a second portion 199 of the current flows from the active electrode through the second fissure to the ground, thereby simultaneously treating two fissures. This embodiment is advantageous because the simultaneous treatment reduces the treatment time of the disc.

In other embodiments, the HCF may be first heated and then directed to the fissured portion of the collagen. In preferred embodiments thereof, the device comprises a bipolar RF frequency electrode and a pump. The bipolar RF frequency electrode heats the HCF to a therapeutic treatment temperature, and the pump then directs the heated HCF to the target site.

In some embodiments involving the treatment of a ruptured annulus, the nucleus pulposus material located on the outside of the disc is removed prior to application of the electrical energy. In other embodiments, a high viscosity HCF is provided in the through hole near the outer wall in order to prevent any leakage of nucleus pulposus material.

EXAMPLE I

This example demonstrates the preferential heating of wounded areas of collagen tissue infused with hypertonic saline over uninfused wounded areas.

Bovine meniscus tissue (a collagen based tissue similar to the collagen in the annulus fibrosus) was obtained and cut into thin strips having a thickness of about 0.8 cm. Two electrode-containing 18 gage needles 201, 202 were placed, inserted into the tissue in a parallel manner about 3 mm below the surface of the tissue to produce a bipolar electrode arrangement.

Small stabs having a diameter of about 1.0 mm and a depth of about 2.0 mm were made into the tissue with an 18 gage hypodermic needle. These stabs (or "wounds") were made to simulate fissures on the inner wall of an annulus fibrosus. About 1 cc of HCF was then infused into the stabs with a 20 gage needle. Excess HCF appearing on the surface of the tissue was removed.

Figure 20:
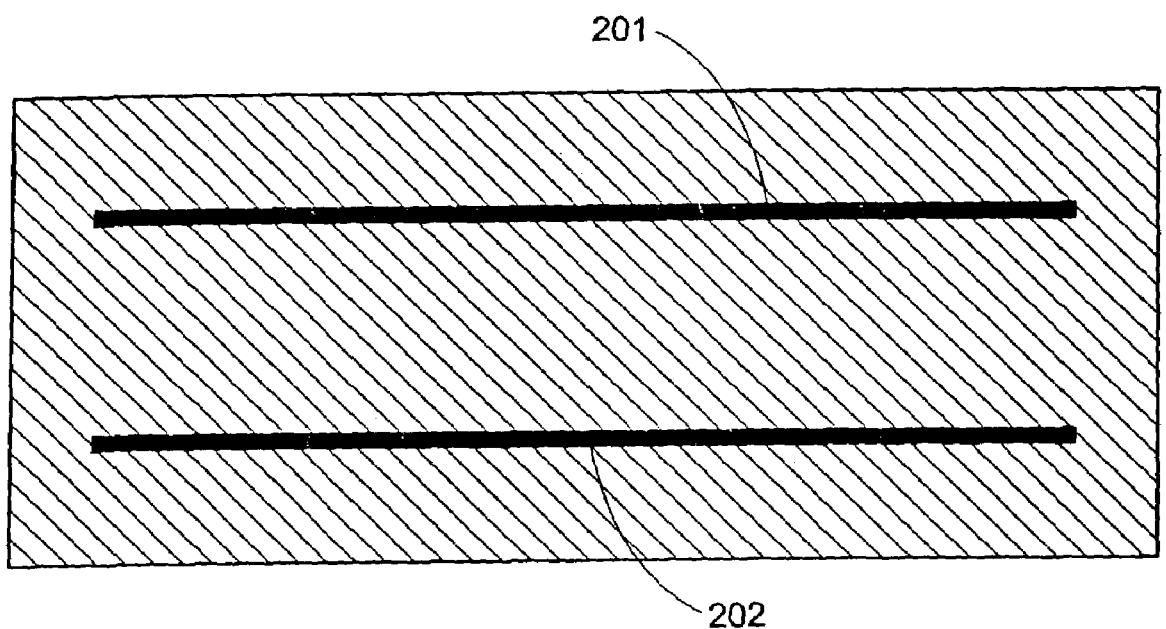
FIG. 20 discloses a representation of the experimental design described in the Examples.

Now referring to FIG. 20, two microthermocouples (T1 and T2) were placed about 2 mm below the surface about halfway between the electrode portions of the needles and at a distance of about 3 cm from each other. In order to record the effect of HCF upon heating, microthermocouple T1 was placed centrally within an HCF-filled wound.

A Force FX generator (Valleylab, Boulder, Colo.) was connected to the first and second electrode and was calibrated to generate 10 watts of power. This low level of power was used to minimize the amount of damage to the tissue. Power was applied in 10 second bursts and temperature measurements were recorded when the power was turned off to minimize artifact.

Figure 21:
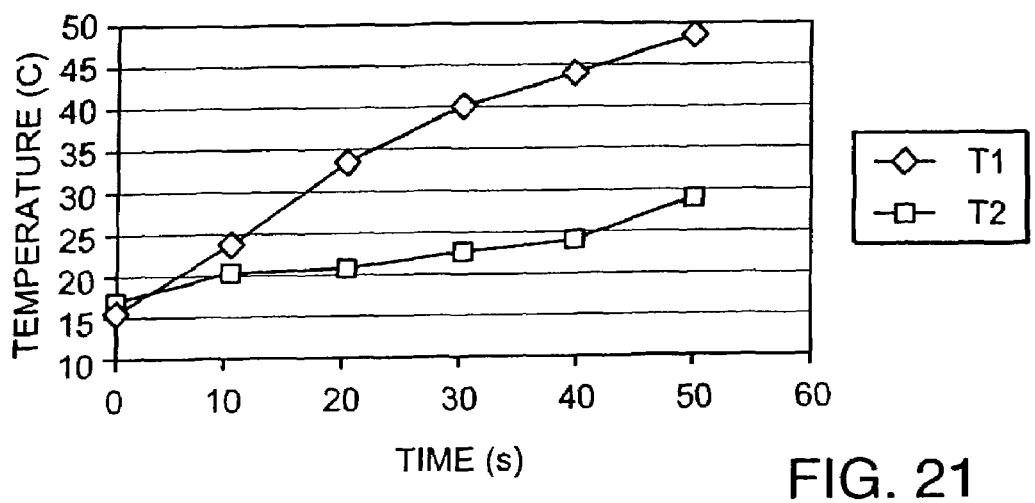
FIGS. 21-23 discloses a graph of the time versus temperature responses of tissue to various experimental setups.

FIG. 21 reports the temperature at sites T1 and T2 as a function of treatment time for this example. As clearly shown by this Figure, the wound infused with HCF was able to be heated to about 50° C. after only about 50 seconds. In contrast, uninfused site T2 was able to be heated to less than about 30° C. after about 50 seconds.

Since it is believed that coagulation of collagen tissue begins to occur at about 65° C., this example demonstrates that preferential heating of areas infused with HCF allows coagulation temperatures to be achieved within surgically desirable time frames. Without wishing to be tied to a theory, it is believed that power is preferentially deposited in the fissure containing the HCF.

EXAMPLE II

This example demonstrates the preferential heating of wounded areas of collagen tissue infused with hypertonic saline over wounded areas infused with normal saline.

The procedure for this example was substantially similar to that of Example I, except that the wound at the T2 site was infused with isotonic saline (0.9% NaCl).

Figure 22:
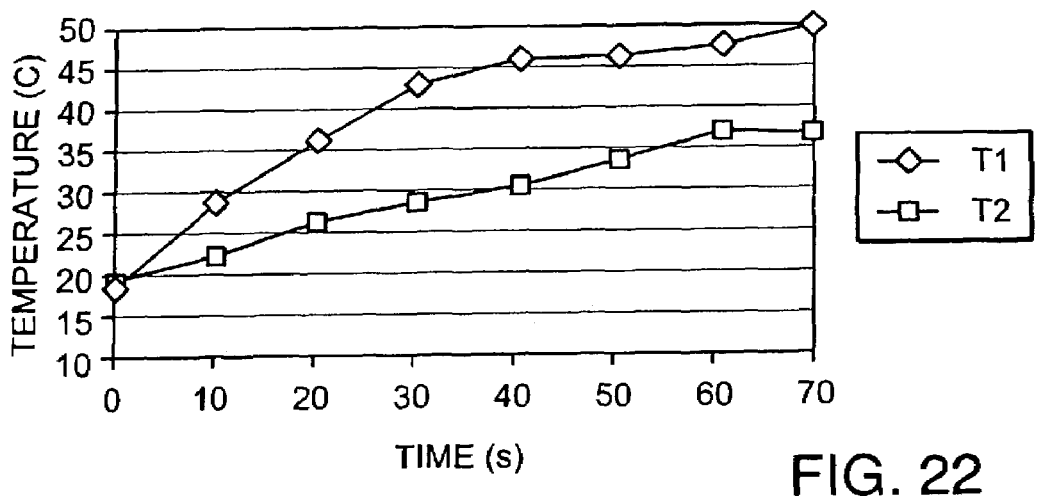

FIG. 22 reports the temperature at sites T1 and T2 as a function of treatment time for this example. As clearly shown by this Figure, the wound infused with HCF was again able to be heated to over 45° C. after only about 50 seconds, and about 50° C. after only about 70 seconds. In contrast, the T2 site infused with isotonic saline was able to be heated to less than about 30° C. after about 50 seconds, and only about 35° C. after about 70 seconds.

It is noted that the temperature rise provided by isotonic saline in this example (about 33° C. at 50 seconds) is only a marginal improvement over the temperature rise experienced at the uninfused site in Example I (about 29° C. at 50 seconds). Accordingly, it is clear that the use of an HCF provides an advantage.

COMPARITIVE EXAMPLE

The procedure for this example was substantially similar to that of Example I, except that none of the wounds were infused.

Figure 23:
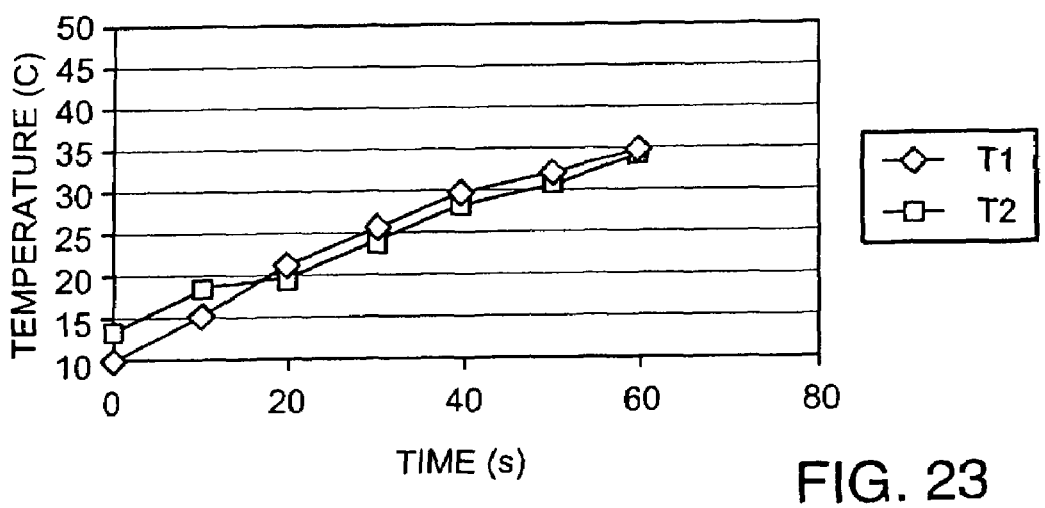

FIG. 23 reports the temperature at sites T1 and T2 as a function of treatment time for this example. As clearly shown by this Figure, the temperature rises at these uninfused sites are substantially similar to the temperature rise found at the uninfused T2 site of Example I.

When the above Examples and Comparitive Examples are evaluated, it is evident that the practice of the present invention provides the surgeon with two distinct advantages:

First, practice of the present invention will allow the surgeon (or practitioner) to raise the temperature of a volume of collagen tissue within the annulus fibrosus to at least 45° C. in less than one minute. This allows the surgeon to quickly begin coagulation or denervation of the target tissue.

Therefore, in accordance with one embodiment of the present invention, there is provided a method of therapeutically treating an intervertebal disc having an annulus fibrosus, comprising the steps of:

a) providing an energy device having an active electrode and a return electrode,
b) positioning the device adjacent the annulus fibrosus,
c) applying a sufficiently high frequency voltage difference between the active and return electrodes to generate a current therebetween to raise the temperature of a volume within the annulus fibrosus to at least 45° C. in less than one minute.

Second, practice of the present invention allows the surgeon to raise the temperature of a volume of collagen tissue located within the annulus fibrosus of the disc at a depth of more than 5 mm to at least 45° C. This allows the surgeon to coagulate or denervate tissue deep within the annulus fibrosus.

Therefore, in accordance with one embodiment of the present invention, there is provided a method of therapeutically treating an intervertebal disc having an annulus fibrosus, comprising the steps of:

a) providing an energy device having an active electrode and a return electrode,
b) positioning the device adjacent the annulus fibrosus,
c) applying a sufficiently high frequency voltage difference between the active and return electrodes to generate a current therebetween and raise the temperature of a volume located within the annulus fibrosus at a depth of more than 5 mm to at least 45° C.

The following relates to the general structure of preferred energy devices in accordance with the present invention:

The apparatus according to the present invention comprises an electrosurgical probe having a shaft with a proximal end, a distal end, and at least one active electrode at or near the distal end. A connector is provided at or near the proximal end of the shaft for electrically coupling the active electrode to a high frequency voltage source. In some embodiments, a return electrode coupled to the voltage source is spaced a sufficient distance from the active electrode to substantially avoid or minimize current shorting therebetween and to shield the return electrode from heating through a larger surface area. The return electrode may be provided integral with the shaft of the probe or it may be separate from the shaft (e.g., on a liquid supply instrument). In preferred cases, the return electrode defines an inner passage for flow of electrically conducting liquid therethrough. The liquid is directed through the return electrode and over the active electrode to thereby provide a return current flow path between the tissue target site and the return electrode.

In preferred embodiments, the electrosurgical probe or catheter will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

Preferably, the shaft may be a flexible catheter that is introduced through a percutaneous penetration in the patient. However, for endoscopic procedures within the spine, the shaft will have a suitable diameter and length to allow the surgeon to reach the target site (e.g., a disc) by delivering the shaft through the thoracic cavity, the abdomen or the like. Thus, the shaft will usually have a length in the range of about 5.0 to 30.0 cm, and a diameter in the range of about 0.2 mm to about 10 mm. In any of these embodiments, the shaft may also be introduced through rigid or flexible endoscopes.

In an alternative embodiment, the probe may comprise a long, thin needle (e.g., on the order of about 1 mm in diameter or less) that can be percutaneously introduced through the patient's back directly into the spine. The needle will include one or more active electrode(s) for applying electrical energy to tissues within the spine. The needle may include one or more return electrode(s), or the return electrode may be positioned on the patient's back, as a dispersive pad. In either embodiment, sufficient electrical energy is applied through the needle to the active electrode(s) to either shrink the collagen fibers within the spinal disc, or to denervate nerves within the disc.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

In some embodiments, the electrically conductive wires may run freely inside the catheter bore in an unconstrained made, or within multiple lumens within the catheter bore.

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

Temperature probes associated with the apparatus may preferably be disposed on or within the electrode carrier; between the electrodes (preferred in bipolar embodiments); or within the electrodes (preferred for monopolar embodiments). In some embodiments wherein the electrodes are placed on either side of the fissure, a temperature probe is disposed between the electrodes and is adapted so as to be deployable into the fissure. In preferred embodiments, the deployable portion of the temperature probe comprises a memory metal.

The electrode terminal(s) are preferably supported within or by an inorganic insulating support positioned near the distal end of the instrument shaft. The return electrode may be located on the instrument shaft, on another instrument or on the external surface of the patient (i.e., a dispersive pad). The close proximity of nerves and other sensitive tissue in and around the spinal cord, however, makes a bipolar design more preferable because this minimizes the current flow through non-target tissue and surrounding nerves. Accordingly, the return electrode is preferably either integrated with the instrument body, or another instrument located in close proximity thereto. The proximal end of the instrument(s) will include the appropriate electrical connections for coupling the return electrode(s) and the electrode terminal(s) to a high frequency power supply, such as an electrosurgical generator.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. To increase flexibility, electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes. In other embodiments, the probe can be sectored so that a given circumference comprises an electrode region and an inactive region. In some embodiments, the inactive region is masked.

The return electrode is typically spaced proximally from the active electrode(s) a suitable distance to avoid electrical shorting between the active and return electrodes in the presence of electrically conductive fluid. In most of the embodiments described herein, the distal edge of the exposed surface of the return electrode is spaced about 0.5 to 25 mm from the proximal edge of the exposed surface of the active electrode(s), preferably about 1.0 to 5.0 mm. Of course, this distance may vary with different voltage ranges, conductive fluids, the electrode geometry and depend on the proximity of tissue structures to active and return electrodes. The return electrode will typically have an exposed length in the range of about 1 to 20 mm.

The application of a high frequency voltage between the return electrode(s) and the electrode terminal(s) for appropriate time intervals effects modifying the target tissue. In some embodiments of the present invention, the tissue volume over which energy is dissipated (i.e., a high current density exists) may be more precisely controlled, for example, by the use of a multiplicity of small electrode terminals whose effective diameters or principal dimensions range from about 10 mm to 0.01 mm, preferably from about 2 mm to 0.05 mm, and more preferably from about 1 mm to 0.1 mm. In this embodiment, electrode areas for both circular and non-circular terminals will have a contact area (per electrode terminal) below 50 mm$^2$ for electrode arrays and as large as 75 mm$^2$ for single electrode embodiments. In multiple electrode array embodiments, the contact area of each electrode terminal is typically in the range from 0.0001 mm$^2$ to 1 mm$^2$, and more preferably from 0.001 mm$^2$ to 0.5 mm$^2$. The circumscribed area of the electrode array or electrode terminal is in the range from 0.25 mm$^2$ to 75 mm$^2$, preferably from 0.5 mm$^2$ to 40 mm$^2$. In multiple electrode embodiments, the array will usually include at least two isolated electrode terminals, often at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

In a preferred aspect of the invention, the active electrode comprises an electrode array having a plurality of electrically isolated electrode terminals disposed over a contact surface, which may be a planar or non-planar surface and which may be located at the distal tip or over a lateral surface of the shaft, or over both the tip and lateral surface(s). The electrode array will include at least two and preferably more electrode terminals, and may further comprise a temperature sensor. In a preferred aspect, each electrode terminal will be connected to the proximal connector by an electrically isolated conductor disposed within the shaft. The conductors permit independent electrical coupling of the electrode terminals to a high frequency power supply and control system with optional temperature monitor for operation of the probe. The control system preferably incorporate active and/or passive current limiting structures, which are designed to limit current flow when the associated electrode terminal is in contact with a low resistance return path back to the return electrode.

The use of such electrode arrays in electrosurgical procedures is particularly advantageous as it has been found to limit the depth of tissue necrosis without substantially reducing power delivery. The voltage applied to each electrode terminal causes electrical energy to be imparted to any body structure which is contacted by, or comes into close proximity with, the electrode terminal, where a current flow through all low electrical impedance paths is preferably but not necessarily limited. It will be appreciated that such low impedance paths generally occur when an electrode terminal does not contact or come into close proximity with the body structure, but rather is in contact with a low impedance environment, such as the saline, or other electrolyte being introduced past the return electrode. The presence of an electrolyte provides a relatively low impedance path back to the common or return electrode.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes, twizzle shapes, spring shapes, twisted metal shapes, annular or solid tube shapes or the like. Alternatively, the electrode(s) may comprise a plurality of filaments, rigid or flexible brush electrode(s), side-effect brush electrode(s) on a lateral surface of the shaft, coiled electrode(s) or the like.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. Provision of the electrically conductive fluid around the target site also helps to maintain the tissue temperature at desired levels.

The voltage difference applied between the return electrode(s) and the electrode terminal(s) will be at high or radio frequency, typically between about 50 kHz and 20 MHz, usually being between about 100 kHz and 2.5 MHz, preferably being between about 400 kHz and 1000 kHz, often less than 600 kHz, and often between about 500 kHz and 600 kHz. The RMS (root mean square) voltage applied will usually be in the range from about 5 volts to 1000 volts, preferably being in the range from about 10 volts to 200 volts, often between about 20 to 100 volts depending on the electrode terminal size, the operating frequency and the operation mode of the particular procedure. Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak. As discussed above, the voltage is usually delivered continuously with a sufficiently high frequency (e.g., on the order of 50 kHz to 20 MHz) (as compared with e.g., lasers claiming small depths of necrosis, which are generally pulsed about 10 to 20 Hz). In addition, the sine wave duty cycle (i.e., cumulative time in any one-second interval that energy is applied) is preferably on the order of about 100% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the power level according to the specific requirements of a particular procedure.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 µH to 50,000 µH, depending on the electrical properties of the target tissue, the desired tissue heating rate and the operating frequency. Alternatively, capacitor-inductor (LC) circuit structures may be employed, as described previously in U.S. Pat. No. 5,697,909. Additionally, current limiting resistors may be selected. Preferably, microprocessors are employed to monitor the measured current and control the output to limit the current.

A portion of the current flow path between the electrode terminals and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, hypotonic saline or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood or intracellular saline, may be sufficient to establish a portion of the conductive path between the return electrode(s) and the electrode terminal(s). However, conductive fluid that is introduced into the patient is generally preferred over blood because blood will tend to coagulate at certain temperatures. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal(s). This ensures that the instrument will not be activated when conductive fluid is not present, minimizing the tissue damage that may otherwise occur.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

We claim:

1. A method of therapeutically treating an intervertebal disc having a nucleus pulposus and an annulus fibrosus having a fissure having a width and defining first and second adjacent collagen tissue regions, comprising the steps of:
   a) adding a hyperconductive fluid to the fissure,
   b) positioning a first electrode adjacent to the hyperconductive fluid, and
   c) applying a sufficiently high frequency voltage difference between the first electrode and a second electrode to generate a current through the hyperconductive fluid sufficient to preferentially resistively heat the conductive fluid and thereby conductively heat the adjacent collagen tissue regions to therapeutically coagulate or denervate at least a portion of the adjacent collagen tissue regions.

2. The method of claim 1 wherein an RF energy device comprises the first electrode.

3. The method of claim 2 wherein the RF energy device further comprises a second electrode, and wherein the first and second electrodes form an active electrode and a return electrode.

4. The method of claim 3 wherein the first electrode is positioned within an inner portion of the nucleus pulposus.

5. The method of claim 3 wherein the fissure has a mouth located adjacent an inner portion of the annulus fibrosus, and each of the first and second electrodes are positioned at the mouth of the fissure so that current flows substantially only within the fissure and preferentially resistively heats the hyperconductive fluid.

6. The method of claim 5 wherein the first and second electrodes are separated to define a spacing, and the spacing is less than the width of the fissure.

7. The method of claim 3 wherein the first electrode is the active electrode, the second electrode is the return electrode, and the active and return electrodes are separated to define a spacing of between 5.1 mm and 10 mm.

8. The method of claim 3 wherein the first electrode is the active electrode and has a surface area of between 3 mm$^2$ and 15 mm$_2$.

9. The method of claim 8 wherein the second electrode is a return electrode and has a surface area of between 3 mm$_2$ and 15 mm$_2$.

10. The method of claim 9 wherein the ratio of the active electrode surface area to the return electrode surface area is between 1:1 and 3:1.

11. The method of claim 2 wherein the RF energy device is monopolar having an active electrode and a ground electrode.

12. The method of claim 11 wherein the active electrode is positioned within an outer portion of the nucleus pulposus.

13. The method of claim 11 wherein the fissure has a mouth located adjacent an inner portion of an annulus fibrosus portion of the disc, and the active electrode is positioned adjacent the mouth.

14. The method of claim 1 wherein the hyperconductive fluid comprises an organic compound.

15. The method of claim 1 wherein the hyperconductive fluid is aqueous.

16. The method of claim 15 wherein the hyperconductive fluid further comprises a salt.

17. The method of claim 16 wherein the salt comprises a positive species selected from the group consisting of Na, K, Ca and Mg.

18. The method of claim 16 wherein the salt comprises Na.

19. The method of claim 16 wherein the salt comprises a negative species selected from the group consisting of Cl and SO$_4$.

20. THe method of claim 16 wherein the salt is present in the hyperconductive fluid at a concentration of from 1% to saturation.

21. The method of claim 16 wherein the salt is present in the hyperconductive fluid at a concentration of from 3% to saturation.

22. The method of claim 16 wherein the salt is present in the hyperconductive fluid at a concentration of from 21% to saturation.

23. The method of claim 1 wherein the hyperconductive fluid has a viscosity at least 10% greater than that of isotonic saline.

24. The method of claim 1 wherein the hyperconductive fluid comprises a gel.

25. The method of claim 24 wherein the gel is fibrin based.

26. The method of claim 1 wherein the hyperconductive fluid has a volume of between 1 cc and 2 cc.

27. The method of claim 1 further compising the step of:
d) removing a portion of the nucleus pulposus.

28. The method of claim 27 wherein step d) is performed prior to step a).

29. The method of claim 1 wherein the step d) heats a portion of the fluid to a temperature of between 45° C. and 90° C.

30. The method of claim 1 wherein the step d) heats a portion of the fluid to a temperature of between 60° C. and 70° C.

31. The method of claim 1 wherein the step d) heats a portion of the fluid to a temperature of between 60° C. and 65° C.

32. The method of claim 31 wherein step d) is performed in less than 8 minutes.

33. The method of claim 1 the hyperconductive fluid further comprises a contrast agent.

34. A method of therapeutically treating an intervertebal disc having an annulus fibrosus, comprising the steps of:
a) providing an energy device having an active electrode and a return electrode,
b) positioning the device adjacent the annulus fibrosus,
c) adding a hyperconductive fluid to the annulus fibrosus, and
d) applying a sufficiently high frequency voltage difference between the active and return electrodes to generate a current therebetween to preferentially resistively heat the conductive fluid and thereby conductively heat the annulus fibrosus to raise the temperature of a volume within the annulus fibrosus to at least 45° C. in less than one minute to coagulate or denervate the annulus fibrosus.

35. A method of therapeutically treating an intervertebal disc having an annulus fibrosus, comprising the steps of:
a) providing an energy device having an active electrode and a return electrode,
b) positioning the device adjacent the annulus fibrosus,
c) adding a hyperconductive fluid to the annulus fibrosus, and
d) applying a sufficiently high frequency voltage difference between the active and return electrodes to generate a current therebetween to preferentially resistively heat the conductive fluid and thereby conductively heat the annulus fibrosus and raise the temperature of a volume located within the annulus fibrosus at a depth of more than 5 mm to at least 45° C. to coagulate or denervate the annulus fibrosus.

36. A method of therapeutically treating a herniation in an annulus fibrosus of an intervertebral disc, the herniation having a fissure having a mouth and first and second ends defining a diameter and a periphery, comprising the steps of:
a) providing an energy device having an active electrode and a return electrode,
b) positioning the device at the mouth of the fissure so that the active electrode is adjacent the first end of the herniation and the second electrode is adjacent the second end of the herniation,
c) adding a hyperconductive fluid to the fissure,
d) applying a sufficiently high frequency voltage difference between the active and return electrodes to generate a current therebetween flowing from the first end of the herniation along the periphery of the herniation to the second end of the herniation to preferentially resistively heat the conductive fluid and thereby conductively heat the herniation and to coagulate or denervate the herniation.

37. A method of therapeutically treating a fissure in an annulus fibrosus of an intervertebral disc, the fissure having a mouth and a width, comprising the steps of:
a) providing a bipolar device having an active electrode and a return electrode, the electrodes being spaced at a first distance, the first distance being less than the width of the fissure,
b) positioning the device adjacent the mouth of the fissure,
c) adding a hyperconductive fluid to the fissure, and
d) applying a sufficiently high frequency voltage difference between the active and return electrode to generate a current therebetween flowing substantially only within the fissure and preferentially heating the hyperconductive fluid to thereby conductively heat the tissue adjacent the fissure to therapeutically coagulate or denervate the tissue adjacent the fissure.

38. A method of therapeutically treating a target tissue within an intervertebral disc, comprising the steps of:
   a) removing a portion of the nucleus pulposus, and
   b) injecting a hyperconductive fluid into the nucleus pulposus, and
   a) passing a current through the hyperconductive fluid to preferentially resistively heat the conductive fluid and thereby conductively heat the nucleus pulposus to coagulate the nucleus pulposus.

39. The method of claim 38 wherein step a) is performed before then step b).

40. A method of therapeutically treating an intervertebal disc having an annulus fibrosus having a fissure defining first and second closely adjacent collagen tissue regions, comprising the steps of:
   a) adding a hyperconductive fluid to the fissure,
   b) positioning a first electrode adjacent to the hyperconductive fluid, and
   c) applying a sufficiently high frequency voltage difference between the first electrode and a second electrode to generate a current flowing preferentially through the hyperconductive fluid to preferentially resistively heat the hyperconductive fluid and thereby conductively heat the adjacent collagen tissue regions to coagulate or denervate the adjacent collagen tissue regions.

41. A method of therapeutically treating an intervertebal disc having an annulus fibrosus having a fissure defining first and second closely adjacent collagen tissue regions, comprising the steps of:
   a) adding a hyperconductive fluid to the fissure,
   b) positioning a first electrode adjacent to the hyperconductive fluid, and
   c) applying a sufficiently high frequency voltage difference between the first electrode and a second electrode to generate an increased current flowing through the hyperconductive fluid to preferentially resistively heat the hyperconductive fluid and thereby conductively heat the adjacent collagen tissue regions to coagulate or denervate the adjacent collagen tissue regions.

42. A method of therapeutically treating an intervertebal disc having an annulus fibrosus having a fissure defining first and second adjacent collagen tissue regions, comprising the steps of:
   a) adding a hyperconductive fluid to the fissure,
   b) positioning a first electrode adjacent to the hyperconductive fluid, and
   c) applying a sufficiently high frequency voltage difference between the first electrode and a second electrode to generate an increased current flowing through the adjacent collagen tissue regions to preferentially resistively heat the hyperconductive fluid and thereby conductively heat the adjacent collagen tissue regions to coagulate or denervate the adjacent collagen tissue regions.

43. A method of therapeutically treating an intervertebal disc having an annulus fibrosus having a fissure defining first and second adjacent collagen tissue regions having open porosity, comprising the steps of:
   a) adding a hyperconductive fluid to the fissure and the open porosity of the adjacent collagen tissue regions,
   b) positioning a first electrode adjacent to the hyperconductive fluid, and
   c) applying a sufficiently high frequency voltage difference between the first electrode and a second electrode to generate an current flowing substantially only through the fissure and the open porosity of the adjacent collagen tissue regions to preferentially resistively heat the hyperconductive fluid and thereby conductively heat the adjacent collagen tissue regions to coagulate or denervate the adjacent collagen tissue regions.

* * * * *